United States Patent
Gilbert et al.

[11] Patent Number: 6,133,273
[45] Date of Patent: Oct. 17, 2000

[54] PYRAZOLOPYRIMIDINE-2,4-DIONE SULFONAMIDES

[75] Inventors: Adam Matthew Gilbert, Congers, N.Y.; Zhen-jia Chen, Bothell, Wash.; Gerardo De La Cruz Francisco, Orangeburg, N.Y.; Magda Asselin, Mahwah, N.J.

[73] Assignee: American Home Products Corporation, Madison, N.J.

[21] Appl. No.: 09/304,180

[22] Filed: May 3, 1999

Related U.S. Application Data

[60] Provisional application No. 60/122,063, May 8, 1998.

[51] Int. Cl.[7] ................... A61K 31/4162; C07D 487/04
[52] U.S. Cl. ............................................. 514/258; 544/262
[58] Field of Search ............................... 544/262; 514/258

[56] References Cited

U.S. PATENT DOCUMENTS

| | | | |
|---|---|---|---|
| 4,663,326 | 5/1987 | Hamilton | 544/262 |
| 5,409,934 | 4/1995 | Smith et al. | 544/267 |

FOREIGN PATENT DOCUMENTS 242044 of 1987 Germany.

OTHER PUBLICATIONS

Bilezikian, J.P., Fert. Menopausal Studies, 41, 148–155 (1996).
Rico, H. et al., Calcif, Tissue Int. 56, 181–185 (1995).
Kappe et al., J. Chem. Soc. Perkins Trans. I, 1342–1344 (1991).
Papesch et al., J. Org. Chem. 30, 199 (1965).
Azev et al., Mendeleev Commn. 229–231 (1995).
An. Farm. Quim. Sao Paulo, 20, 78–85 (1980).
Senga et al., J. Heterocycl. Chem. 15, 359–363 (1978).
Senga et al., Synthesis, 176–177 (1977).
Senda et al., Chem. Pharm. Bull., 20, 391–398 (1972).

*Primary Examiner*—Mukund J. Shah
*Assistant Examiner*—Venkataraman Balasubramanian
*Attorney, Agent, or Firm*—Rebecca R. Barrett

[57] ABSTRACT

A compound of formula (I)

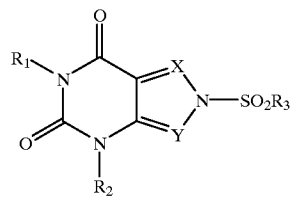

(I)

wherein:

X=N and Y=CH or X=CH and Y=N $R_1$ and $R_2$ are independently, straight chain alkyl of 2 to 12 carbon atoms, branched chain alkyl of 3 to 10 carbon atoms, cycloalkyl of 3 to 10 carbon atoms, aryl of 4 to 10 carbon atoms, 4 to 10 membered heteroaryl or a moiety of the formula $(CH_2)_m$-A wherein m is 1 to 9 and A is cycloalkyl of 3 to 7 carbon atoms; and $R_3$ is a straight chain alkyl of 1 to 12 carbon atoms, branched chain alkyl of 3 to 10 carbon atoms, aryl of 4 to 10 carbon atoms or 4 to 10 membered heteroaryl for use in the treatment of disorders associated with bone loss by increased transcription and elevation of plasma calcitonin levels.

26 Claims, No Drawings

PYRAZOLOPYRIMIDINE-2,4-DIONE SULFONAMIDES

BACKGROUND OF INVENTION

This application claims the benefit of U.S. Provisional Application No. 60/122,063, filed May 8, 1998.

Calcitonin is a 32 amino acid polypeptide hormone secreted by the parafollicular or C cells of the thyroid gland in response to elevated blood levels of calcium. This hormone decreases blood calcium (hypocalcemic activity) primarily by inhibiting bone resorption through plasma membrane-associated receptors on the osteoclast. High-turnover bone loss, as seen with hypercalcemia of malignancy, estrogen withdrawal as following the onset of the menopause, and certain anti-inflammatory or arthritis therapies, has recently been shown to be preventable by the administration of calcitonin (Bilezikian, J. P., *J. Fert. Menopausal Studies.* 1996, 41, 148–155). As recently demonstrated for post-menopausal osteoporosis, treatment leads to not only a maintenance of bone mass and total body calcium, but also to decreases in the incidence of hip and vertebral fractures (Rico, H., et al., *Calcif. Tissue Int.* 1995, 56, 181–185, Gennari, C., *Aust. Family Physician.* 1994, 48, 196–200). Thus, it is apparent that calcitonin is an appropriate therapeutic for the prevention and treatment of osteoporosis by virtue of its hypocalcemic activity.

Although calcitonin has demonstrated efficacy in the prevention of high-turnover bone loss, a limitation for its wide-spread use is the lack of oral bioavailability, necessitating administration by parental (intra-muscular) or nasal routes. However, stimulation of endogenous calcitonin synthesis and release by inducer compounds would be expected to result in a similar therapeutic effect. Therefore, this invention describes the ability of a series of pyrazolopyridine-2,4-dione sulfonamides to induce the expression and release of endogenous calcitonin.

Hamilton discloses a class of 5-substituted pyrazolo[4,3-d]pyrimidine-2,4-diones for use as cardiotonics and for reversing bronchoconstriction in U.S. Pat. No. 4,663,326. Dorn et al. disclose a series of alkoxycarbonyl-amido methoxypyrazoles as cardiovascular agents in German Patent Application DD 242044. Smith discloses a class of xanthine derivatives which inhibit phosphodiesterase (PDEV) in U.S. Pat. No. 5,409,934.

The synthesis of variously substituted pyrazolo[4,3-d]pyrimidine-2,4-diones are described in the following publications: from 5-carboalkoxy-6-diazidouracils (Kappe et al. *J. Chem. Soc., Perkin Trans.* 1 1991, 1342–4); from 6-methyluracils (Papesch et al. *J. Org. Chem.* 1965, 30, 199).

Gauri et al. disclose a class of 6-alkyl pyrazolo[3,4-d]pyrimidine-2,4-diones useful as phosphodiesterase inhibitors, bronchospasmolytics and retinotripics in European Patent Application EP 63381

The synthesis of variously substituted pyrazolo[3,4-d]pyrimidine-2,4-diones are described in the following publications: from 6-phenyl-1,2,4-triazine 4-oxide and 1,3-dimethyluracil-6-hydrazones (Azev et al. *Mendeleev Commun.* 1995, 229–31); from 6-hydrazinyluracils (*An. Farm. Quim. Sao Paulo* 1980, 20, 78–85); from 1,3-dimethyl-6-hydrazinouracil with DMF dialkyl acetals (Senga et al. *J. Heterocycl. Chem.* 1978, 15, 359–63); from 6-hydrazinyluracils (Senga et al. *Synthesis* 1977, 399–403; Senda et al. *Chem. Pharm. Bull* 1972, 20, 391–398; Senda et al. *Chem. Pharm. Bull.* 1972, 20, 176–7).

DESCRIPTION OF THE INVENTION

The present invention relates to pyrazolopyrimidine-2,4-dione sulfonamides having pharmacological activity, and to their use in the treatment of disorders associated with bone loss by increased transcription and elevation of plasma calcitonin levels. Such disorders include, but are not limited to: Paget's Disease, post menopausal osteoporosis, senile osteoporosis, and glucocorticoid-induced osteoporosis.

In accordance with this invention there, is provided a group of compounds represented by the formula (I):

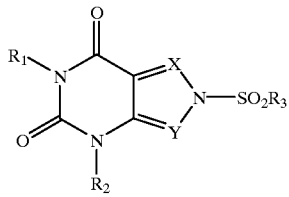

$R_1$ and $R_2$ are independently, straight chain alkyl of 2 to 12 carbon atoms, branched chain alkyl of 3 to 10 carbon atoms, cycloalkyl of 3 to 10 carbon atoms, aryl of 4 to 10 carbon atoms, 4 to 10 membered heteroaryl or a moiety of the formula $(CH_2)_m$-A wherein m is 1 to 9 and A is cycloalkyl of 3–7 carbon atoms; and $R_3$ is a straight chain alkyl of 1 to 12 carbon atoms, branched chain alkyl of 3 to 10 carbon atoms, aryl of 4 to 10 carbon atoms or 4 to 10 membered heteroaryl, or a pharmaceutically acceptable salt thereof.

In preferred aspects of the invention are provided compounds of formula (I) wherein $R_1$ and $R_2$ are independently, straight chain alkyl of 2 to 8 carbon atoms, branched chain alkyl of 3 to 8 carbon atoms or a moiety of the formula $(CH_2)_m$-A wherein m is 1 to 5 and A is a cycloalkyl of 3 to 7 carbon atoms; and $R_3$ is a straight chain alkyl of 1 to 8 carbon atoms, branched chain alkyl of 3 to 8 carbons atoms, aryl of 4 to 10 carbon atoms, 4 to 10 membered heteroaryl; or a pharmaceutically acceptable salt thereof.

In still more preferred aspects of the invention are provided compounds of formula (I) wherein $R_1$ and $R_2$, are independently, straight chain alkyl of 3 to 6 carbon atoms or branched chain alkyl of 3 to 6 carbon atoms; and $R_3$ is a straight chain alkyl of 3 to 6 carbons, aryl of 4 to 10 carbon atoms or 4 to 10 membered heteroaryl; or a pharmaceutically acceptable salt thereof.

Alkyl, whether used alone or as part of another group (i.e. alkoxy) include straight and branched chain alkyl groups containing from 1 to 12 carbon atoms. For example, methyl, ethyl, propyl, isopropyl, butyl and t-butyl are encompassed by the term alkyl. In some embodiments of the present invention alkyl may refer to substituted or unsubstituted alkyl. Carbon number refers to carbon backbone and does not include carbon atoms of substitutions such as alkoxy substitutions and the like.

Halogen, as used herein means chlorine, bromine, iodine and fluorine.

Aryl, as used herein refers to single or multiple 4 to 10 membered aromatic ring radicals including but not limited to phenyl, benzyl, naphthalene, anthracene, phenanthrene, indene and indacene. Preferred are phenyl, benzyl and napthalene. In some embodiments of the present invention the aryl group may be substituted.

Heteroaryl as used herein refers to single or multiple 4 to 10 membered aromatic ring radicals having from 1 to 3 heteroatoms selected from S, O, or N including, but not limited to, furan, thiophene, pyrrole, imidazole, oxazole, thiazole, isoxazole, pyrazole, isoxazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine and isobenzofuran. Preferred hetroaryls include furan, thiophene, pyrrole, imidazole, oxazole, thiazole, isoxazole, pyrazole, isoxazole, isothiazole, oxadiazole, triazole, thiadiazole, quinolizine, quinoline, and isoquinoline. More preferred heteroaryls include furan, thiophene, imidazole, isoxazole, quinoline and pyrazole. In some embodiments of the present invention the heteroaryl group is substituted.

Preferably, the substituted aryl group is substituted with from 1 to 3 groups. The substituted heteroaryl group is preferably substituted with 1 to 3 groups, and preferably 1 or 2 groups. Alkyl and cycloalkyl groups may also be substituted. Suitable substitutions include, but are not limited to halogen, alkyl, alkoxy, haloalkyl, haloalkoxy, hydroxy, nitro, nitrile, amino, cyano, carboxy, alkoxycarbonyl, alkylcarbonyl, alkoxycarbonylalkyl and alkylcarbonyloxy.

The most preferred compounds of the present invention are:

4,6-dibutyl-3-chloropropanesulfonyl-2,4-dihydro-pyrazolo [4,3-d]pyrimidine-5,7-dione;
4,6-dibutyl-2-phenylmethanesulfonyl-2,4-dihydro-pyrazolo [4,3-d]pyrimidine-5,7-dione;
4,6-dibutyl-2-(3-trifluoromethyl-benzenesulfonyl)-2,4-dihydro-pyrazolo[4,3-d]-pyrimidine-5,7-dione;
4,6-dibutyl-2-(2-naphthalenesulfonyl)-2,4-dihydro-pyrazolo[4,3-d]pyrimidine-5,7-dione;
4,6-dibutyl-2-(4-tert-butyl-benzenesulfonyl)-2,4-dihydro-pyrazolo[4,3-d]pyrimidine-5,7-dione;
4,6-dibutyl-2-(4,5-dichloro-thiophene-2-sulfonyl)-2,4-dihydro-pyrazolo[4,3-d]-pyrimidine-5,7-dione;
4,6-dibutyl-2-(4[1,3-dimethyl-5-chloropyrazolsulfonyl)-2,4-dihydro-pyrazolo[4,3-d]-pyrimidine-5,7-dione;
4,6-dibutyl-1-(3,5-dimethyl-isoxazole-4-sulfonyl)-1,4-dihydro-pyrazolo[4,3-d]-pyrimidine-5,7-dione;
4,6-dibutyl-1-(propane-1-sulfonyl)-1,4-dihydro-pyrazolo[4,3-d]pyrimidine-5,7-dione;
4,6-dibutyl-1-ethanesulfonyl-1,4-dihydro-pyrazolo[4,3-d] pyrimidine-5,7-dione;
4,6-dibutyl-2-(2,4,6-trichloro-benzenesulfonyl)-2,4-dihydro-pyrazolo[4,3-d]-pyrimidine-5,7-dione;
4,6-dibutyl-2-(quinoline-8-sulfonyl)-2,4-dihydro-pyrazolo [4,3-d]pyrimidine-5,7-dione;
5,7-dibutyl-2-(3-chloro-propane-1-sulfonyl)-2,7-dihydro-pyrazolo[3,4-d]pyrimidine-4,6-dione;
5,7-dibutyl-2-(4-trifluoromethoxy-benzenesulfonyl)-2,7-dihydro-pyrazolo[3,4-d]-pyrimidine-4,6-dione;
5,7-dibutyl-2-(4,5-dichloro-thiophene-2-sulfonyl)-2,7-dihydro-pyrazolo[3,4-d]-pyrimidine-4,6-dione;
5,7-dibutyl-2-(4-trifluoromethyl-benzenesulfonyl)-2,7-dihydro-pyrazolo[3,4-d]-pyrimidine-4,6-dione;
5,7-dibutyl-2-methanesulfonyl-2,7-dihydro-pyrazolo[3,4-d] pyrimidine-4,6-dione;
4-butyl-2-(3-chloro-propane-1-sulfonyl)-6-methyl-2,4-dihydro-pyrazolo[4,3-d]-pyrimidine-5,7-dione;
5,7-dibutyl-2-phenylmethanesulfonyl-1,7-dihydro-pyrazolo [3,4-d]pyrimidine-4,6-dione;
6-butyl-2-(3-chloro-propane-1-sulfonyl)-4-(3-methyl-butyl)-2,4-dihydro-pyrazolo-[4,3-d]pyrimidine-5,7-dione; and
2-(3-chloro-propane-1-sulfonyl)-5,7-bis-cyclopropylmethyl-2,7-dihydro-pyrazolo-[3,4-d] pyrimidine-4,6-dione, and pharmaceutical salts thereof.

It is understood that the definition of the compounds of formula (I), when $R_1$, $R_2$ or $R_3$ contain asymmetric carbons, encompass all possible stereoisomers and mixtures thereof which possess the activity discussed below. In particular, the definition of formula (I) encompasses racemic modifications and any optical isomers which possess the indicated activity. Optical isomers may be obtained in pure form by standard separation techniques.

Pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R_1$, $R_2$ or $R_3$ contain a carboxyl group, salts of the compounds of this invention may be formed with bases such as alkali metals (Na, K, Li) or the alkaline earth metals (Ca or Mg).

As mentioned previously, the compounds of formula (I) have been found to increase transcription and elevate plasma levels of calcitonin. They are therefore useful in the treatment of disorders associated with high turnover bone loss, such as Paget's Disease, post menopausal osteoporosis, senile osteoporosis, and glucocorticoid-induced osteoporosis. The present invention accordingly provides a pharmaceutical composition which comprises a compound of this invention in combination or association with a pharmaceutically acceptable carrier.

The compositions are preferably adapted for oral or subcutaneous administration. However, they may be adapted for other modes of administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as fillers, disintegrating agents, binders, lubricants, flavoring agents and the like. They are formulated in conventional manner, for example, in a manner similar to that use for known antihypertensive agents, diuretics and β-blocking agents.

Generally, the compounds of Formula I are conveniently synthesized as described below.

In accordance with the present invention, compounds of Formula (I), where X is N, Y is CH and $R_1$ and $R_2$ are the same moiety, may be prepared according to the following Scheme I.

Scheme I

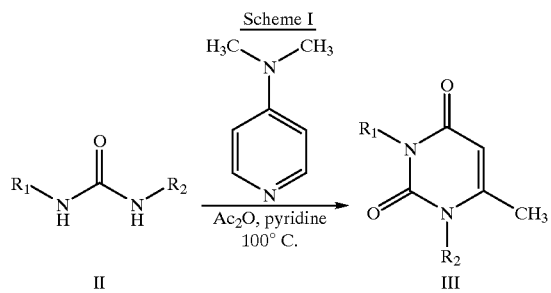

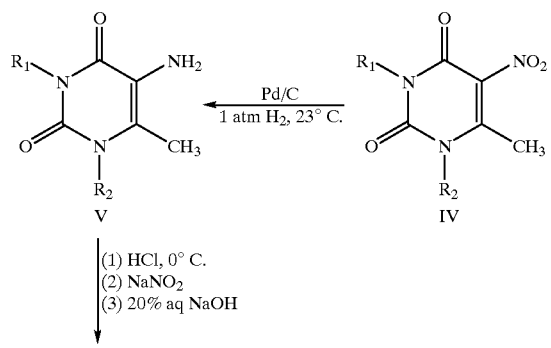

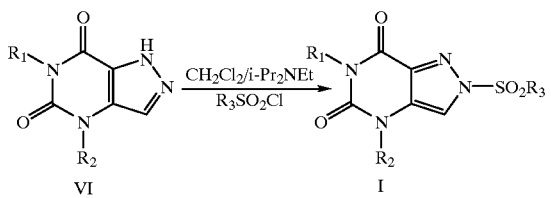

Thus, known compound of Formula II is reacted with dimethylaminopyridine in acetic anhydride and pyridine at 100° C. to give a compound of Formula III in accordance with the procedure described by Egg and Volgger, *Synthesis* 1982, 1071. The compound of Formula III is treated with concentrated sulfuric acid at 0° C. followed by the addition of fuming $HNO_3$ to effect nitration and give the compound of Formula IV. The compound of Formula V is obtained as the product of catalytic hydrogenation of the compound of Formula IV using a suitable catalyst such as Pd/C in suitable solvent such as an alcohol including, but not limited to ethanol. Cyclization to compound of Formula VI can be realized by treatment in HCl and dropwise addition of sodium nitrite. The solution is added to 20% aqueous sodium hydroxide. The compound of Formula VI is treated with methylene chloride and diisopropylethylamine in the presence of the sulfonylchloride derivative of $R_3$ to afford a compound of Formula I.

Further in accordance with the invention compounds of Formula I where X is N, Y is CH and $R_1$ and $R_2$ are different entities may be prepared in accordance with Scheme II as follows.

Scheme II

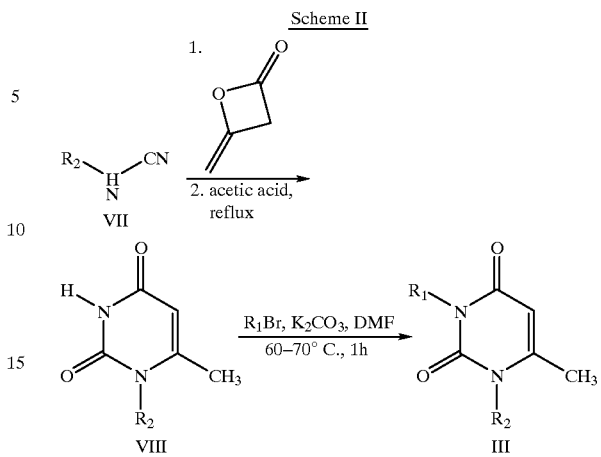

Thus, known compound of Formula VII is reacted with diketene and acetic acid to afford compound of Formula VIII as described by Kato, et al., *Chem. Pharm Bull.* 1981 29, 862. A compound of Formula VIII is reacted with halogenated $R_1$ in the presence of pottassium carbonate in dimethylformamide (DMF) at 60–70° C. for about one hour until the starting material is consumed to provide a compound of Formula III. Thereafter, the reaction proceeds as described for Scheme I.

Alternatively, $R_1$ may be added first by reaction of a compound of Formula IX in ethylacetate, hydrochloric acid, sulfuric acid, and ethanol for 6 to 7 days followed by additions of sodium hydroxide and hydrochloric acid to afford a compound of Formula X as described by Muraoka, et al., *Chem. Pharm. Bull.* 1970,18, 261.

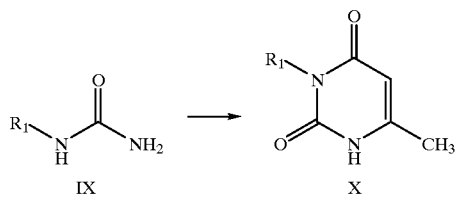

Thereafter compound of Formula X is reacted with halogenated $R_2$ as described in Scheme II to afford compound of Formula III and the reaction proceeds as described for Scheme I.

Compounds of Formula (I) where X is CH, Y is N and $R_1$ and $R_2$ are the same moiety may be synthesized in accordance with Scheme III as follows.

Scheme III

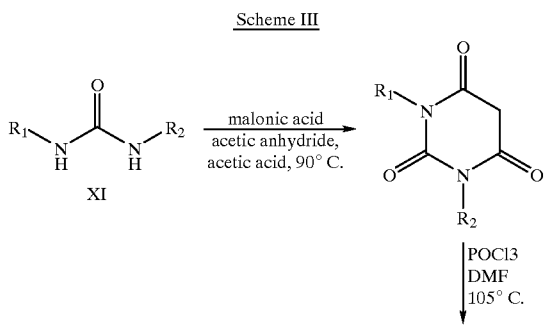

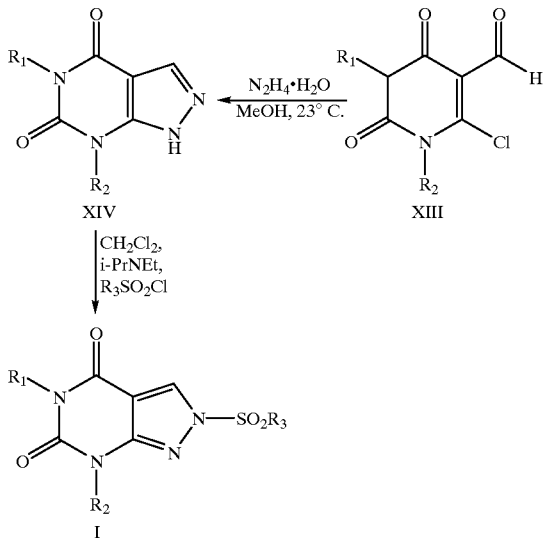

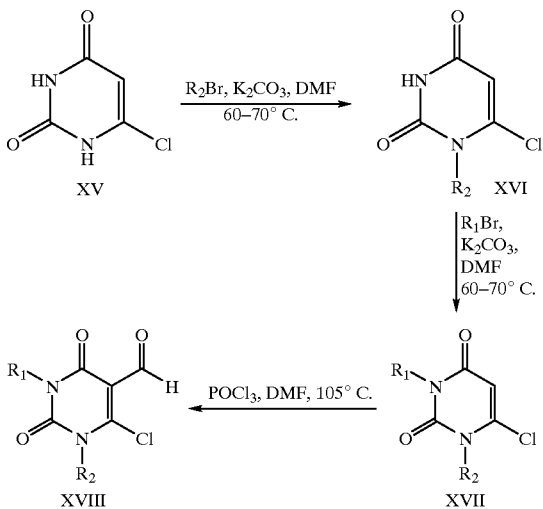

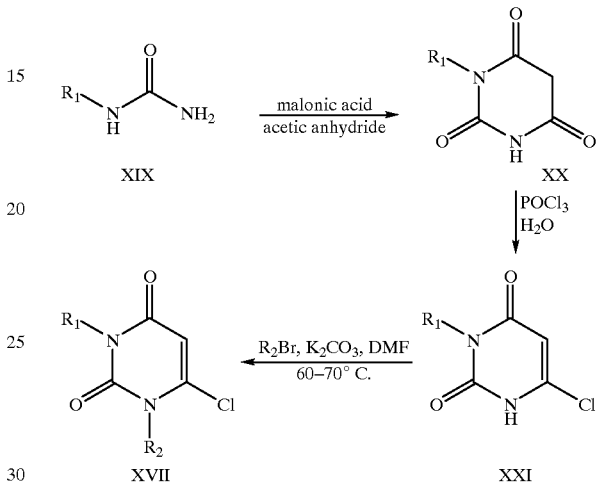

Thus, cyclization of known compound of Formula XI is achieved with malonic acid, acetic anhydride and acetic acid at about 90° C. as described in Goldner et al., *Just. Liebigs. Ann. Chem.* 1966, 691, 142 to afford a compound of Formula XII. A compound of formula XIII is prepared by treatment of compound of Formula XII with phosphoryltrichloride (POCl$_3$) in DMF at about 105° C. as described by Furukawa, et al., EP 0166054. Thereafter, the cyclization of compound of Formula XIII is realized in accordance with the procedure of Hirota, et al., *S. Chem. Pharm. Bull.* 1983, 31, 3959 by the addition of N$_2$H$_4$ and methanol at 23° C. to afford a compound of Formula XIV. The final product, a compound of Formula I is prepared by treatment of compound of Formula XIV with methylene chloride and diisopropylethylamine in the presence of the sulfonylchloride derivative of R$_3$.

Where X is CH, Y is N and R$_1$ and R$_2$ are not the same moiety, two procedures may be followed. First, where R$_2$ is attached first, compounds are prepared by the method of Scheme IV as follows:

Thus, in accordance with Scheme IV, known compound XV is treated with halogenated R$_2$ in the presence of pottasium carbonate in dimethyl formamide at 60–70° C. according to the procedure of Ishikawa, et al., *Heterocycles* 1990, 31, 1641. The resultant compound of Formula XVI is similarly treated with halogenated R$_1$ to afford compound of Formula XVII. The compound of Formula XVII is treated with phosphoryltrichloride in DMF at 105° C. to form the compound of Formula XVIII. The final product is prepared as described in Scheme III.

Finally, where R$_1$ is attached first, compounds of Formula I are prepared by the method of Scheme V as follows:

Cyclization of known compound of Formula XIX is performed by treatment with malonic acid and acid anhydride to afford compound of Formula XX in accordance with procedure of Bilitz, et al., *Chem. Ber.* 1921, 54, 1035. Thereafter, compound of Formula XX is treated with phosphoryltrichloride and water for about one hour as taught by Meueller, et al., *J. Med. Chem.* 1993, 36, 3441 to afford compound of Formula XXI. Compound of Formula XXI is treated with halogenated R$_2$ in the presence of pottasium carbonate in dimethylformamide at 60–70° C. for one hour to afford compound of Formula XVII. Compound of Formula XVII is treated as described above for Scheme IV to arrive at compounds of Formula I.

The present invention further provides a compound of the invention for use as an active therapeutic substance. Compounds of formula (I) are of particular use in the increase of plasma calcitonin levels.

The present invention further provides a method of treating high turnover bone loss in mammals including man, which comprises administering to the afflicted mammal an effective amount of a compound or a pharmaceutical composition of the invention.

The following examples are presented to illustrate rather than limit the present invention.

EXAMPLES

The plasma calcitonin elevation activity of the compounds of this invention was established in accordance with standard pharmaceutically accepted test procedures with representative compounds as follows:

EXAMPLE A

Calcitonin/Luciferase Reporter Gene Expression Assay

This assay was used to determine the ability of a compound to stimulate transcription of a luciferase reporter gene regulated by 3 kb of the promoter region of the human calcitonin gene.

A reporter cell line (designated $C_{1-3}$) was developed by Oncogene Science by stable transfection of a single, unrearranged copy of a calcitonin/luciferase reporter gene construct into the TT human thyroid carcinoma cell line as described in U.S. Pat. No. 5,665,543. $C_{1-3}$ cells were plated at a density of 6,500–7,500 cells per well in a 96-plate microtiter plate. Twenty-four to forty-eight hours later, compounds were added to the wells in triplicate. Compounds were tested at a concentration of 10 μg/mL in 0.5% DMSO. Compounds that exhibited a transcription activation ratio (TAR)>1.5 (equivalent to>50% increase in transcription) advanced to primary follow-up (CA-FUP), in which compounds were re-screened at four concentrations: 10 μg/mL, 2 μg/mL, 0.4 μg/mL and 0.08 μg/mL. Controls were distributed throughout the plate, and include 1) unstimulated cells, for basal luciferase expression, 2) cells stimulated with 1 mM 8-CPT-cAMP (expect 2–3 fold induction).

The plates were incubated for 12 hours in a humidified $CO_2$ incubator, washed, and then lysed in luciferase assay buffer as described in U.S. Pat. No. 5,665,543, incorporated by reference herein in its entirety. The production of light is measured on a luminometer.

Calculations

TAR Ratio: Stimulation of calcitonin promoter-dependent transcription is expressed as a ratio of luciferase activity (LUCI) in the presence of test compound compared to the LUCI activity in the untreated control:

$$\frac{\text{LUCI test compound}}{\text{LUCI control}} = \text{TAR}$$

Transcription Activity: Compounds are deemed active if TAR>1.5

The results of this study are shown in Table I.

TABLE I

Calcitonin Promoter/Luciferase Transcription Assay

| Compound | n | TAR (30 μM) |
|---|---|---|
| Example 1 | 1 | 1.34 |
| Example 2 | 1 | 1.51 |
| Example 3 | 3 | 1.79 |
| Example 4 | 1 | 1.75 |
| Example 5 | 1 | 2.27 |
| Example 6 | 1 | 1.69 |
| Example 7 | 2 | 2.13 |
| Example 8 | 2 | 2.14 |
| Example 9 | 1 | 1.47 |
| Example 10 | 2 | 1.43 |
| Example 11 | 3 | 1.76 |
| Example 12 | 2 | 2.22 |
| Example 13 | 2 | 1.91 |
| Example 14 | 1 | 2.22 |
| Example 15 | 4 | 2.93 |
| Example 16 | 1 | 2.61 |
| Example 17 | 1 | 1.95 |
| Example 18 | 1 | 1.10 |
| Example 19 | 2 | 1.97 |
| Example 20 | 1 | 1.57 |
| Example 21 | 2 | 1.20 |
| Example 22 | 1 | 1.60 |

EXAMPLE B

Calcitonin Secretion/RIA Assay Protocol

This assay was used to determine the ability of a compound to increase the amount of calcitonin secreted by the $C_{1-3}$ cell line.

A calcitonin RIA kit (Nichols Institute Diagnostics, Kit # 40-2125) was used in accordance with manufacturer's suggestions as summarized below:

Materials

Cell Line: $C_{1-3}$ (Parent Cell Line: TT-medullary thyroid carcinoma),

Reagents:

Reagent A—(Anti-Calcitonin)

Reagent B—($^{125}$I-Calcitonin)

Regent C—(Anti-Goat Precipitant)

Regent D—(Zero Standard).

Reagents E–I—(Calcitonin Standards)

Reagents J–K (Calcitonin Controls: Level and Level 2)

Reagent L—(NSB Buffer)

Procedure

1. Glass tubes were labeled to include Total Count (TC), Nonspecific Binding (NSB), Maximum Binding (Bo), Standards, Controls and Patient Sera in duplicate.
2. 300 mL of Standard Zero (Reagent D) was added to tubes 3 through 6 (NSB and Bo).
3. 300 mL of Standards* (Reagents E-1) was added to tubes 7–16 as follows:
   Tubes 7 & 8 Standard E 4 pg/mL
   Tubes 9 & 10 Standard F 10 pg/mL
   Tubes 11 & 12 Standard G 20 pg/mL
   Tubes 13 & 14 Standard H 40 pg/mL
   Tubes 15 & 16 Standard I 80 pg/mL
4. 300 mL of Patient Serum 1 was added to tubes 21 and 22, Patient Serum 2 was added to tubes 23 and 24, etc.
5. 100 mL of Reagent L (NSB Buffer) was added to tubes 3 and 4.
6. 100 mL of Reagent A (Anti-Calcitonin) was added to all tubes except tubes 1 & 2 (TC) and tube 3 & 4 (NSB). All tubes were vortexed, covered with parafilm or foil and incubated 44±6 hours at 2–8° C.
7. 100 mL of 125|Calcitonin (Reagent B) was added to all tubes. All tubes were vortexed, covered with parafilm or foil and incubated 22±3 hours at 2–8° C.
8. Reagent C (Anti-Goat Precipitant) was mixed gently but thoroughly by inverting the vial several times before use. 1 mL Reagent C was added to all tubes except 1 and 2 (TC). Tubes were vortexed and incubated 20 minutes at room temperature.
9. All tubes were centrifuged at 1300–1500×g for 15 minutes at 2–8° C.
10. Supernatant was decanted immediately after centrifugation taking care to leave the precipitate intact.
11. Tubes were counted 4 minutes or longer.

Calculations

Secretion Ratio: Stimulation of calcitonin secretion is expressed as a ratio of secretion activity in the presence of test compound compared to the secretion activity in the untreated control:

$$\frac{\text{Secretion activity test compound}}{\text{Secretion activity control}} = \text{Secretion Ratio}$$

Secretion Activity: Compounds were designated active if Secretion Ratio>2.5.

TABLE II

Calcitonin Secretion/RIA Assay

| Compound | n | Secretion Ratio (30 μM) |
|---|---|---|
| Example 1 | 1 | 4.35 |
| Example 2 | 1 | 2.55 |
| Example 3 | 1 | 3.79 |
| Example 4 | 1 | 4.91 |
| Example 5 | 1 | 4.50 |
| Example 6 | 1 | 3.40 |
| Example 7 | 1 | 2.92 |
| Example 8 | 1 | 3.23 |
| Example 9 | 1 | 2.71 |
| Example 10 | 1 | 2.90 |
| Example 11 | 1 | 4.31 |
| Example 12 | 1 | 3.83 |
| Example 13 | 1 | 2.71 |
| Example 14 | 1 | 4.29 |
| Example 15 | 1 | 3.67 |
| Example 16 | 1 | 3.86 |
| Example 17 | 1 | 3.93 |
| Example 18 | 1 | 1.38 |
| Example 19 | 1 | 3.43 |
| Example 20 | 1 | 2.25 |
| Example 21 | 1 | 1.02 |
| Example 22 | 1 | 2.93 |

EXAMPLE C

Serum Calcium/Plasma Calcitonin Determination Assay

This assay was used to evaluate the ability of a test compound to decrease serum calcium and increase plasma calcitonin in rats using either an acute or sub-acute protocol.

Acute Administration Study: After 72 hours acclimatization, young male or female Sprague Dawley rats weighing 170–250 g were randomly divided in groups of 8. The rats were fasted and given deionized $H_2O$ 18 hours prior to the start of the study. The purpose of the fasting is to reduce the variability in serum calcium and plasma calcitonin levels. Each rat is weighed.

The dosing regimen was as follows:

| Group | Treatment | Dose[b] | Route[c] |
|---|---|---|---|
| A | Vehicle (1 % Tween 80 in saline) | 0.1 mL/100 g/day | ip or sc |
| B | Salmon Calcitonin | 5 IU/rat/day | sc |
| C–G | Test Compounds | 30 mg/kg/day | ip or sc |

[b]Single administration at time = 0
[c]sc administration is a single injection or is done continuously via a mini-pump At different intervals between 10 min and 6 h after dosing (usually 1 to 3 time points), 0.5 mL of blood was collected from each rat under ketamine/acepromazine anesthesia via the tail vein, subclavean artery, jugular vein or (terminal via) cardiac puncture. Serum was evaluated for total calcium and plasma was evaluated for calcitonin. After the final bleeding, the rats were euthanized humanely (by over exposure to $CO_2$).

Subacute Administration Study: After 72 hours acclimatization, young male or female Sprague Dawley rats weighing 170–250 g were randomly divided in groups of 8. The rats were fasted and given deionized $H_2O$ 18 hours prior to the start of the study. The purpose of the fasting is to reduce the variability in serum calcium and plasma calcitonin levels. Each rat was weighed.

The dosing regimen was as follows:

| Group | Treatment | Dose[b] | Route[c] |
|---|---|---|---|
| A | Vehicle (1 % Tween 80 in saline, corn oil or $H_2O$) | 0.1 mL/100 g/2x/day | ip or sc |
| B | Salmon Calcitonin | 5 IU/rat/day | sc |
| C–G | Test Compounds | 30 mg/kg/2x/day | ip or sc |

[b]In vehicle and test compound groups, the treatments that the animals received varied from one to twice a day and from time = 0 to time = 5 days. The rats are fasted and given deionized $H_2O$ 18 hours prior to the last administration of test compounds. The purpose of the fasting is to reduce the variability in serum calcium and plasma calcitonin levels.
[c]sc administration is a single injection or is done continuously via a mini-pump At different intervals between 10 min and 6 h after dosing (usually 1 to 3 time points), 0.5 mL of blood was collected from each rat under ketamine/acepromazine anesthesia via the tail vein, subclavean artery, jugular vein or (terminal via) cardiac puncture. Serum was evaluated for total calcium and plasma was evaluated for calcitonin. After the final bleeding, the rats were euthanized humanely (by over exposure to $CO_2$).

Measurements: Body weight, serum calcium levels and plasma calcitonin levels.

Data Evaluations: The difference in serum calcium and plasma calcitonin between a treatment group and the vehicle group was determined using a one-way analysis of variance with Dunnett's test, or other multiple comparison methods. Compounds were designated active if $p<0.05$ vs. vehicle value.

TABLE IV

Acute/Subacute Hypocalcemia and Plasma Calcitonin Studies[a]

| Compound | n | Acute/ Subacute | % Decrease Serum Calcium | % Increase Plasma Calcitonin |
|---|---|---|---|---|
| Example 4 | 8 | Subacute | 5* | 8 |
| Example 5 | 8 | Subacute | 1 | 101* |
| Example 6 | 8 | Subacute | 0 | 12 |
| Example 7 | 8 | Subacute | 4* | 80* |

[a]all compounds administered sc
*$p < 0.05$ vs. vehicle value

EXAMPLE D

Inhibition of Phosphodiesterase IV (PDE-IV) Isolated from Human U937 Cells

This assay was used to biochemically assess the ability of a test compound to inhibit PDE-IV isolated from a U937 cell line, where PDE-IV refers to the cGMP-insensitive, cAMP-selective PDE.

Cell Culture: U937 cells were grown in RPMI 1640 medium supplemented with 10% heat-inactivated fetal calf serum and Penicillin/Streptomycin (100 units/100 μg per mL) in a humidified 5% $CO_2$ atmosphere at 37° C. Starter cells were maintained in continuous logarithmic growth by seeding them in 75 $cm^2$ vented tissue culture flasks at a concentration of $3\times10^4$ cells/mL and passing them every 3–4 days when the cells reached approximately $8\times10^5$ cells/mL. For experiments, 3–4 day starter cells were seeded in 225 $cm^2$ flasks at $1\times10^5$ cells/mL and harvested 3–4 days later at approx. $6\times10^5$ cells/mL.

Isolation of PDE-IV: U937 cells were activated with 10 μM dibutyryl cAMP for a period of 4 hours (to up-regulate PDE-IV) and then harvested by centrifugation at 1200×g for 10 min in 250 mL conical centrifuge tubes. The pellet from each 200 mL flask was resuspended in 5 mL buffer A [10 mM Tris-HCl, 5 mM MgCl$_2$, 4 mM EGTA, 5 mM 2-mercaptoethanol, 1 μM leupeptin, 1 μM pepstatin A, and 5 μM phenylmethyl sulfonyl fluoride (PMSF) (pH 7.8)], and the cells were lysed using 3 cycles of freezing (3 min in dry ice/acetone) followed by thawing (warm water). The extract was centrifuged for 20 min. at 1200×g to remove cell debris and the supernatant was immediately loaded onto a 1.6×70 cm DEAE-Sepharose CL-6B anion exchange column equilibrated with buffer A. The column was next washed with 2.5 column volumes of buffer B [10 mM Tris-HCl, 5 mM 2-mercaptoethanol, 0.1 μM leupeptin, 0.1 μM pepstatin A and 0.1 μM PMSF (pH 7.8)], and PDEs were eluted with a step gradient consisting of 80 mL each of buffer B containing 0.4 M or 0.7 M sodium acetate (80 mL/hour, 8 mL/fraction). To determine which families of PDEs were present, fractions may be assayed for hydrolytic activity with 1 μM [$^3$H]-cAMP or 1 μM [$^3$H]-cGMP. Additionally, 1 μM [$^3$H]-cAMP assays were conducted in the presence of 10 μM rolipram, 10 μM cGMP, or calmodulin (1 unit/0.4 mL plus 10 μM CaCl$_2$).

When prepared in this manner, approximately 80% of total cAMP PDE activity is eluted by Buffer B containing 0.7 M sodium acetate. This PDE activity consists of >90% PDE-IV (as evidenced by its susceptibility to inhibition by rolipram.

PDE assay: PDE activity was measured using a modification of the radioisotope procedure previously described by Thompson et al. (Thompson, W. J., Terasaki, W. L., Epstein, P. M. and Strada, S. J. *Adv, Cyclic Nucleotide Res.* 1979, 10, 69). Reaction mixtures (0.4 mL) contain 40 mM Tris-HCl (pH 7.8), 4 mM 2-mercaptoethanol, 5 mM MgCl$_2$, 0.1 μM leupeptin, 0.1 μM pepstatin A, 0.1 μM PMSF, 1 μM [3H]-cAMP or 1 μM [$^3$H]-cGMP (~200,000 DPM), and enzyme to initiate the reaction. $^3$H-cAMP substrate was prepared as follows: A stock solution of $^3$H-cyclic nucleotide (1000 μCi/mL) was diluted 1:10 in 50% EtOH. 200 μl of this diluted stock solution was added to a cold (unlabeled) cyclic nucleotide solution, made at a concentration of 4 μM. 100 μl of this solution was used per assay tube to achieve a final concentration of 1 μM cyclic nucleotide per assay tube (200,000 DPM). Enzyme activity was determined at 37° C. Reactions were terminated by boiling, incubating with snake venom, and cooling as previously described (Thompson et al., 1979). The reaction mixture was applied to a (0.8×8.5 cm) column containing 0.4 g Dowex I-X8 affinity resin; reaction tubes were rinsed with 0.5 mL of methanol; and this, along with an extra 1 mL of methanol, was applied to the column to elute the $^3$H-reaction products. After all liquid has passed through the column, the column was plunged with a 12 cc syringe plunger. Each column's eluate was collected in a 20 mL scintillation vial containing 10 mL aquasol-2 and counted by scintillation spectrophotometry. [$^3$H]-adenosine or [$^3$H]-guanosine recovery was corrected for background DPM determined in the absence of enzyme. The amount of enzyme and duration of assay were adjusted to ensure that less than 25% of the substrate was consumed under these conditions. PDE activities of U937 cell PDE-IV preparations have been found to linear for at least 30 minutes. To test inhibition of PDE-IV, a test compounds was added to the reaction mixture, at concentrations ranging from 0.001 μM to 10 μM.

Measurements: Inhibition by a test compound was measured as a percent reduction of total PDE activity, and calculated as follows:

$$\frac{A}{B} \times 100 = \text{PERCENT INHIBITION OF PDE-IV}$$

where A is the PDE activity (mean DPM-background DPM) in the presence of test compound, and B is the total PDE-IV activity (mean DPM-background DPM) in the absence of test compound. These percent inhibition of PDE IV values were normalized to rolipram where the rolipram percent inhibition of PDE IV is set to 0%.

IC$_{50}$s are then estimated by linear regression analysis using the percent inhibition data bracketing 50% inhibition.

TABLE V

Phosphodiesterase IV Inhibitory Activity

| Compound | n | % Inhibition of PDE IV (normalized to rolipram) |
|---|---|---|
| Example 1 | 1 | 31 |
| Example 2 | 1 | 35 |
| Example 3 | 2 | 68 |
| Example 4 | 1 | 33 |
| Example 5 | 1 | 63 |
| Example 6 | 1 | 100 |
| Example 8 | 1 | 26 |
| Example 9 | 1 | 27 |
| Example 10 | 1 | 45 |
| Example 11 | 1 | 26 |
| Example 12 | 1 | 41 |
| Example 13 | 1 | 34 |
| Example 14 | 1 | 92 |
| Example 15 | 3 | 59 |
| Example 16 | 1 | 62 |
| Example 17 | 1 | 17 |
| Example 18 | 1 | 34 |
| Example 19 | 1 | 48 |
| Example 20 | 1 | 42 |
| Example 21 | 1 | 68 |
| Example 22 | 1 | 30 |

Hence, the compounds of this invention have a pronounced effect on increasing both calcitonin transcription and plasma calcitonin levels and are useful in the treatment of disorder associated with high turnover bone loss, such as Paget's Disease, post menopausal osteoporosis, senile osteoporosis, and glucocorticoid-induced osteoporosis as mentioned above, by administration, orally parenterally, or by aspiration to a patient in need thereof. In addition, these compounds are moderate to weak inhibitors of PDE IV, and biological effects associated with inhibiting this phosphodiesterase should not be seen on compound administration.

EXAMPLE 1

4,6-Dibutyl-3-chloropropanesulfonyl-2,4-dihydro-pyrazolo[4,3-d]pyrimidine-5,7-dione

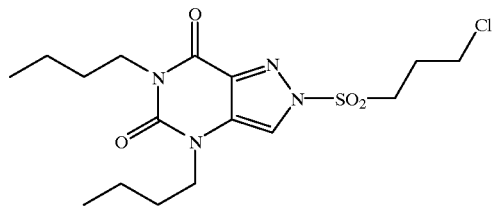

To 222 mg (0.84 mmol) of 4,6-dibutyl-1,4-dihydro-pyrazolo[4,3-d]pyrimidine-5,7-dione in 10 mL CH$_2$Cl$_2$ was added 0.22 mL (163 mg, 1.26 mmol) of i-Pr$_2$NEt followed by 0.11 mL (164 mg, 0.924 mmol) of 3-chloro-n-propanesulfonyl chloride. The resulting solution was stirred at 23° C. for 16 h after which time TLC shows that all starting material had been consumed. The reaction mixture was poured into brine, extracted with 2×50 mL EtOAc, and the combined organics were washed with 1×50 mL brine, dried over MgSO$_4$, filtered and evaporated to a yellow solid. Flash chromatography on silica gel, eluting with CH$_2$Cl$_2$/EtOAc (40/1 to 20/1) gave the title compound. Recrystallization from hot hexanes/EtOAc gave 168 mg (0.415 mmol, a 49% yield) of the title compound as a white crystalline solid. mp: 67–68° C.; $^1$H NMR (300 MHz, CDCl$_3$); δ 0.92–1.02 (m, 6H), 1.34–1.49 (m, 4H), 1.56–1.79 (m, 4H), 2.21–2.34 (m, 2H), 3.65 (t, J=6.1 Hz, 2H), 3.79–3.88 (m, 4H), 4.17 (t, J=7.3 Hz, 2H), 7.87 (s, 1H); IR (KBr, cm$^{-1}$): 3137w, 2958w, 1718m, 1677s, 1626w, 1380m, 1166m; MS (ES) m/z (relative intensity): 405 (M$^+$+H, 100); Anal. Calcd. for C$_{16}$H$_{25}$ClN$_4$O$_4$S: C, 47.46; H, 6.22, N, 13.84. Found: C, 46.80; H, 6.06; N, 13.24.

EXAMPLE 2

4,6-Dibutyl-2-phenylmethanesulfonyl-2,4-dihydro-pyrazolo[4,3-d]pyrimidine-5,7-dione

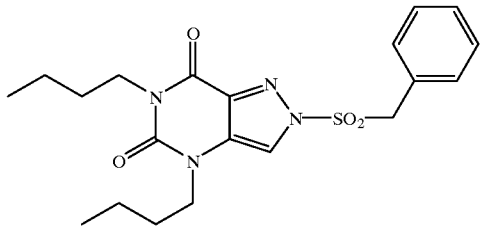

The title compound was synthesized according the procedure of example 1 except that benzylsulfonyl chloride was used in place of 3-chloro-n-propanesulfonyl chloride. Yield: 74%; mp: 90–93° C.; $^1$H NMR (300 MHz, CDCl$_3$); δ 0.89–1.00 (m, 6H), 1.21–1.32 (m, 4H), 1.36–1.53 (m, 2H), 1.59–1.67 (m, 2H), 3.68 (t, J=7.4 Hz, 2H), 4.07 (t, J=7.4 Hz, 2H), 4.84 (s, 2H), 7.08–7.14 (m, 1H), 7.27–7.39 (m, 4H), 7.35 (s, 1H); IR (KBr, cm$^{-1}$): 3136w, 2959m, 2872w, 1723s, 1669s, 1621m, 1386m, 1290m; MS (ES) m/z (relative intensity): 419 (M$^+$+H, 100); Anal. Calcd. for C$_{20}$H$_{26}$N$_4$O$_4$S: C, 57.40; H, 6.26, N, 13.39. Found: C, 58.14; H, 6.54; N, 12.32.

EXAMPLE 3

4,6-Dibutyl-2-(3-trifluoromethyl-benzenesulfonyl)-2,4-dihydro-pyrazolo[4,3-d]pyrimidine-5,7-dione

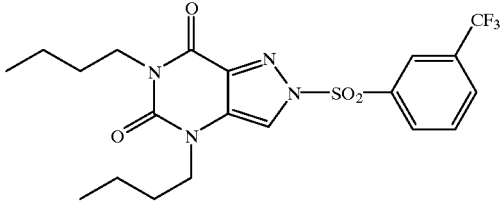

The title compound was synthesized according the procedure of example 1 except that 3-trifluoromethylbenzene chloride was used in place of 3-chloro-n-propanesulfonyl chloride. Yield: 70%; mp: 163–165° C.; $^1$H NMR (300 MHz, CDCl$_3$); δ 0.92 (t, J=7.3 Hz, 3H), 0.99 (t, J=7.3 Hz, 3H), 1.39 (sept, J=7.3 Hz, 4H), 1.53–1.61 (m, 2H), 1.63–1.72 (m, 2H), 3.83 (t, J=7.5 Hz, 2H), 4.00 (t, J=7.5 Hz, 2H), 7.77 (t, J=8.2 Hz, 1H), 7.93 (s, 1H), 7.93–8.00 (m, 1H), 8.27 (d, J=2.0 Hz, 1H), 8.38 (d, J=8.2 Hz, 1H); IR (KBr, cm$^{-1}$): 3134w, 2981w, 1806s, 1755m, 1495w, 1334s, 1194m, 700w; MS (ES) m/z (relative intensity): 473 (M$^+$+H, 100); Anal. Calcd. for C$_{20}$H$_{23}$F$_3$N$_4$O$_4$S: C, 50.84; H, 4.91, N, 11.86. Found: C, 51.08; H, 4.98; N, 11.72.

EXAMPLE 4

4,6-Dibutyl-2-(2-naphthalenesulfonyl)-2,4-dihydro-pyrazolo[4,3-d]pyrimidine-5,7-dione

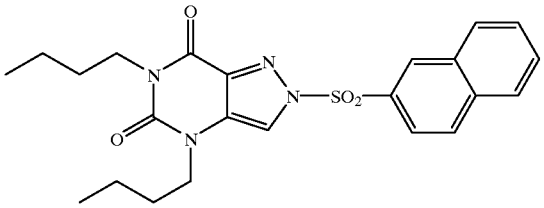

The title compound was synthesized according the procedure of example 1 except that 2-naphthylsulfonyl chloride was used in place of 3-chloro-n-propanesulfonyl chloride. Yield: 78%; mp: 167–168° C.; $^1$H NMR (300 MHz, CDCl$_3$); δ 0.90 (t, J=7.4 Hz, 3H), 0.99 (t, J=7.4 Hz, 3H), 1.21–1.49 (m, 4H), 1.50–1.61 (m, 2H), 1.62–1.63 (m, 2H), 3.82 (t, J=7.5 Hz, 2H), 3.97 (t, J=7.4 Hz, 2H), 7.61–7.78 (m, 2H), 7.92 (d, J=8.2 Hz, 1H), 7.95–8.09 (m, 4H), 8.76 (brs, 1H); IR (KBr, cm$^{-1}$): 3155w, 2960m, 2935m, 2868w, 1720s, 1680s, 1623s, 1384s, 1065s, 668s; MS (ES) m/z (relative intensity): 455 (M$^+$+H, 100); Anal. Calcd. for C$_{23}$H$_{26}$N$_4$O$_4$S: C, 60.78; H, 5.77, N, 12.33. Found: C, 60.63; H, 5.79; N, 12.31.

EXAMPLE 5

4,6-Dibutyl-2-(4-tert-butyl-benzenesulfonyl)-2,4-dihydro-pyrazolo[4,3-d]pyrimidine-5,7-dione

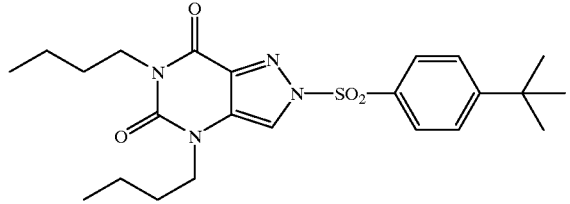

The title compound was synthesized according the procedure of example 1 except that 4-tert-butylbenzenesulfonyl chloride was used in place of 3-chloro-n-propanesulfonyl chloride. Yield: 85%; mp: 158–159° C.; $^1$H NMR (300 MHz, CDCl$_3$); δ 0.91 (t, J=7.3 Hz, 3H), 0.98 (t, J=7.3 Hz, 3H), 1.32 (s, 9H), 1.32–1.43 (m, 4H), 1.54–1.62 (m, 2H), 1.62–1.72 (m, 2H), 3.82 (t, J=7.5 Hz, 2H), 4.11 (t, J=7.4 Hz, 2H), 7.57 (d, J=8.3 Hz, 2H), 7.91 (s, 1H), 8.03 (d, J=8.3 Hz, 2H); IR (KBr, cm$^{-1}$): 3143w, 2960m, 2934m, 2872w, 1721s, 1680s, 1623s, 1385s, 1172s, 1070s; MS (ES) m/z (relative intensity): 461 (M$^+$+H, 100); Anal. Calcd. for C$_{23}$H$_{32}$N$_4$O$_4$S: C, 59.98; H, 7.00, N, 12.16. Found: C, 59.71; H, 6.99; N, 11.93.

EXAMPLE 6

4,6-Dibutyl-2-(4,5-dichloro-thiophene-2-sulfonyl)-2,4-dihydro-pyrazolo[4,3-d]pyrimidine-5,7-dione

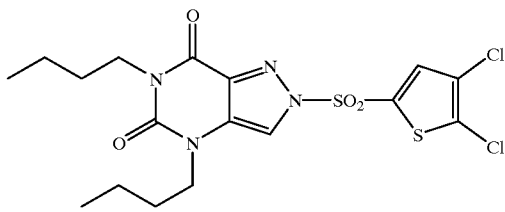

The title compound was prepared according to the procedure of example 1 except that 2,3-dichloro-5-thiophenesulfonyl chloride was used in place of 3-chloro-n-propanesulfonyl chloride. Yield: 76%; mp: 163–166° C.; $^1$H NMR (300 MHz, CDCl$_3$): δ 0.88–1.01 (m, 6H), 1.33–1.48 (m, 4H), 1.57–1.75 (m, 4H), 3.83 (t, J=7.5 Hz, 2H), 4.02 (t, J=7.6 Hz, 2H), 7.78 (s, 1H), 7.86 (s, 1H); IR (KBr, cm$^{-1}$): 3114w, 2957m, 1718s, 1683s, 1626m, 1391s, 1360m, 1190m, 1070m; MS (ES) m/z (relative intensity): 496 (M$^+$+NH$_4$, 100). Anal. Calcd. for C$_{17}$H$_{20}$Cl$_2$N$_4$O$_4$S$_2$: C, 42.59; H, 4.21, N, 11.69. Found: C, 42.62; H, 4.33; N, 11.15.

EXAMPLE 7

4,6-Dibutyl-2-(4[1,3-dimethyl-5-chloropyrazolsulfonyl)-2,4-dihydro-pyrazolo[4,3-d]pyrimidine-5,7-dione

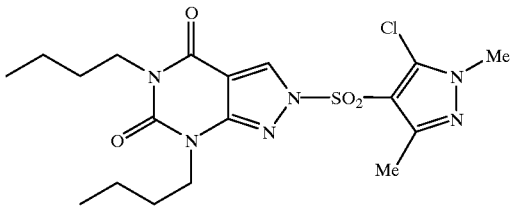

Step 1

6-Amino-1,3-dibutyl-2,4-dioxo-1,2,3,4-tetrahyhdro-pyrimidine-5-carboxaldehyde oxime

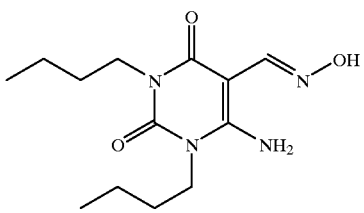

To a suspension of 0.92 g (3.4 mmol) of 6-Amino-5-formyl-1,3-dibutyluracil in 3 mL MeOH was added a solution of 2.0 g (3.4 mol) hydroxylamine hydrochloride in 5 mL of H$_2$O. The mixture was cooled to 0° C. and a solution of 2.2 g (3.4 mmol) of KOH in 5 mL H$_2$O was added in drops. After the addition of complete, the reaction mixture was heated to 60° C. in a closed tube for 12 h. After cooling to 23° C. and diluting with 50 mL H$_2$O, the reaction mixture was extracted with 1×100 mL CH$_2$Cl$_2$, the organics were dried over MgSO$_4$, filtered and evaporated to give 900 mg (3.4 mmol, a 100% yield) of the title compound as a white solid. mp: 145–148° C. $^1$H NMR (300 MHz, DMSO-d$_6$): δ 0.88 (t, J=7.4 Hz, 3H), 0.90 (t, J=7.4, 3H), 1.18–1.37 (m, 4H), 1.37–1.57 (m, 4H), 3.76 (t, J=7.3 Hz, 2H), 3.87 (t, J=7.5 Hz, 2H), 8.23 (s, 1H), 10.49 (s, 1H); IR (KBr, cm$^{-1}$): 3355m, 3161m, 2960w, 1702m, 1620s, 1547m, 1518m, 773w; MS (ES) m/z (relative intensity): 283 (M$^+$+H, 100). Anal. Calcd. for C$_{13}$H$_{22}$N$_4$O$_3$: C, 55.30; H, 7.85; N, 19.84. Found: C, 54.75; H, 8.12; N, 19.54.

Step 2

4,6-Dibutyl-2-(4[1,3-dimethyl-5-chloropyrazolsulfonyl)-2,4-dihydro-pyrazolo[4,3-d]pyrimidine-5,7-dione

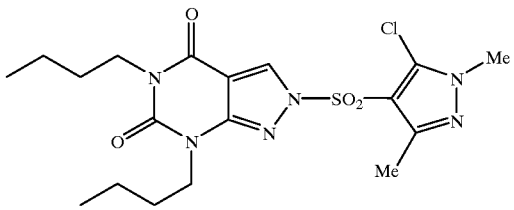

To a 0° C. solution of 3.5 g (12 mmol) of 6-amino-1,3-dibutyl-2,4-dioxo-1,2,3,4-tetrahyhdro-pyrimidine-5-carboxaldehyde oxime in 50 mL CH$_2$Cl$_2$ was added 4.8 g (47.4 mmol) of Et$_3$N, followed by a solution of 6.0 g (26 mmol) of 5-chloro-1,3-dimethylpyrazole-4-sulfonyl chloride in 30 mL CH$_2$Cl$_2$ in drops. The reaction was stirred at 23° C. for 2 h, and diluted with 100 mL CH$_2$Cl$_2$. After washing with brine, the organics were dried over MgSO$_4$, filtered and evaporated to a light yellow oil. Flash chromatography on silica gel, eluting with CH$_2$Cl$_2$, followed 1/1 EtOAc/hexanes, gave 3.24 g (7.09 mmol, a 59% yield) of the title compound as a white solid. mp: 160–163° C.; $^1$H NMR (300 MHz, CDCl$_3$) δ 0.94 (t, J=5.4 Hz, 6H), 1.31–1.37 (m, 4H), 1.57–1.65 (m, 2H), 1.65–1.72 (m, 2H), 2.53 (s, 3H), 3.81 (s, 3H), 3.94–4.00 (m, 4H), 8.59 (s, 1H); IR (KBr, cm$^{-1}$): 2958m, 2934w, 2873w 1777s, 1649s, 1572s, 1399m, 1197, 657m; MS (ES) m/z (relative intensity): 457 (M$^+$+H, 100). Anal. Calcd. for C$_{18}$H$_{25}$ClN$_6$O$_4$S: C, 47.31; H, 5.51; N, 18.39. Found: C, 47.48; H, 5.57; N, 18.70.

EXAMPLE 8

4,6-Dibutyl-1-(3,5-dimethyl-isoxazole-4-sulfonyl)-1,4-dihydro-pyrazolo[4,3-d]pyrimidine-5,7-dione

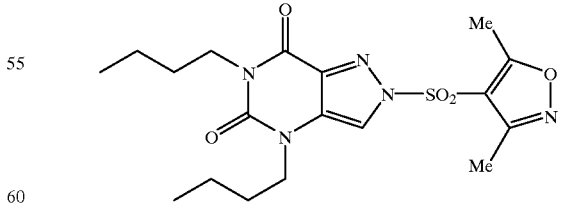

The title compound was prepared according to the procedure of example 1 except that of 3,5-dimethylisoxazole-4-sulfonyl chloride was used in place of 3-chloro-n-propanesulfonyl chloride. Yield: 96%; $^1$H NMR (300 MHz, CDCl$_3$): δ 0.91–1.01 (m, 6H), 1.24–1.45 (m, 4H), 1.56–1.73

(m, 4H), 2.45 (s, 3H), 2.83 (s, 3H), 3.85 (t, J=7.4 Hz, 2H), 4.05 (t, J=7.4 Hz, 2H), 7.89 (s, 1H); IR (KBr, cm$^{-1}$): 3115w, 2959m, 1721s, 1677s, 1621m, 1389m, 1288m, 1205m, 1130m, 1068; MS (ES) m/z (relative intensity): 424 (M$^+$+H, 100). Anal. Calcd. for $C_{18}H_{25}N_5O_5S$: C, 51.05; H, 5.95, N, 16.54. Found: C, 49.89; H, 5.86; N, 15.71

EXAMPLE 9

4,6-Dibutyl-1-(propane-1-sulfonyl)-1,4-dihydro-pyrazolo[4,3-d]pyrimidine-5,7-dione

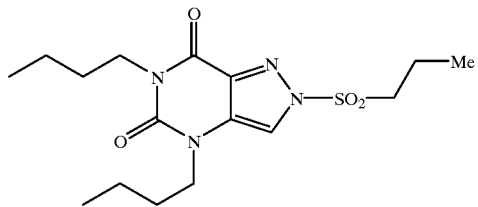

To 500 mg (2.6–2.8 mmol/g resin) of piperidinomethyl polystyrene resin in 25 mL $CH_2Cl_2$ was added 280 mg (1.06 mmol) of 4,6-dibutyl-1,4-dihydro-pyrazolo[4,3-d] pyrimidine-5,7-dione followed by 166 mg (1.17 mmol) of propanesulfonyl chloride. The resulting solution was stirred at 23° C. for 3 h after which time TLC showed that all starting material (4/1 $CH_2Cl_2$/EtOAc; $R_f$=0.15) had been consumed. The reaction mixture was filtered, the filtered cake washed with 3×5 mL $CH_2Cl_2$, and the combined organics were evaporated to give crude yellow oil. Flash chromatography on silica gel, eluting with $CH_2Cl_2$/EtOAc (40/1 to 10/1) gave 359 mg (0.97 mmol, a 92% yield) of the title compound as a yellow solid. mp: 44–48° C.; $^1$H NMR (300 MHz, CDCl$_3$); δ 0.93–1.17 (m, 9H), 1.35–1.44 (m, 4H), 1.61–1.83 (m, 4H), 2.06–2.33 (m, 2H), 3.51–3.68 (m, 2H), 3.85 (t, J=7.5 Hz, 2H), 4.02 (t, J=7.4 Hz, 2H), 7.88 (s, 1H); IR (KBr, cm$^{-1}$): 3231w, 2960m, 1719m, 1675s, 1620m, 1387m, 1289m, 1171m, 1066m; MS (ES) m/z (relative intensity): 371 (M$^+$+H, 100). Anal. Calcd. for $C_{16}H_{26}N_4O_4S$: C, 51.87; H, 7.07, N, 15.12. Found: C, 46.22; H, 6.65; N, 11.91

EXAMPLE 10

4,6-Dibutyl-1-ethanesulfonyl-1,4-dihydro-pyrazolo[4,3-d]pyrimidine-5,7-dione

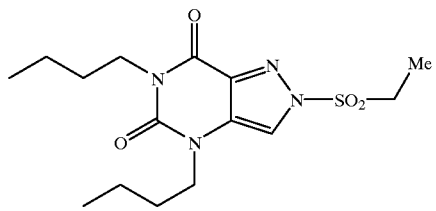

The title compound was prepared according to the procedure of example 9 except that of ethanesulfonyl chloride was used in place of propanesulfonyl chloride. Yield: 46%; mp: 119–121° C.; $^1$H NMR (300 MHz, CDCl$_3$): δ 0.93–1.01 (m, 6H), 1.34 (t, J=7.4 Hz, 3H), 1.36–1.45 (m, 4H), 1.58–1.73 (m, 4H), 3.70 (q, J=7.4 Hz, 2H), 3.85 (t, J=7.5 Hz, 2H), 4.06 (t, J=7.5 Hz, 2H), 7.87 (s, 1H); IR (KBr, cm$^{-1}$): 3136w, 2958w, 1713m, 1665s, 1625m, 1368m, 1288m, 1161m, 1072m; MS (ES) m/z (relative intensity): 357 (M$^+$+H, 100). Anal. Calcd. for $C_{15}H_{24}N_4O_4S$: C, 50.55; H, 6.79, N, 15.72. Found: C, 50.61; H, 6.73; N, 15.45.

EXAMPLE 11

4,6-Dibutyl-2-(2,4,6-trichloro-benzenesulfonyl)-2,4-dihydro-pyrazolo[4,3-d]pyrimidine-5,7-dione

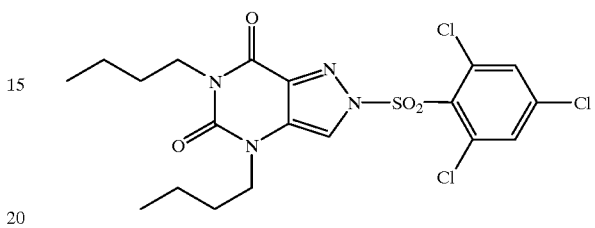

The title compound was prepared according to the procedure of example 9 except that of 2,4,6-trichlorobenzensulfonyl chloride was used in place of propanesulfonyl chloride. Yield: 71%; mp: 89–92° C.; $^1$H NMR (300 MHz, CDCl$_3$): δ 0.91–1.02 (m, 6H), 1.34–1.49 (m, 4H), 1.56–1.76 (m, 4H), 3.87 (t, J=7.5 Hz, 2H), 4.02 (t, J=7.6 Hz, 2H), 7.52 (s, 2H), 8.07 (s, 1H); IR (KBr, cm$^{-1}$): 3112w, 2959w, 1720m, 1677s, 1622m, 1391w, 1288m, 1196m; MS (ES) m/z (relative intensity): 508 (M$^+$+H, 100). Anal. Calcd. for $C_{19}H_{21}Cl_3N_4O_4S$: C, 44.94; H, 4.17, N, 11.03. Found: C, 44.91; H, 4.20; N, 10.72.

EXAMPLE 12

4,6-Dibutyl-2-(quinoline-8-sulfonyl)-2,4-dihydro-pyrazolo[4,3-d]pyrimidine-5,7-dione

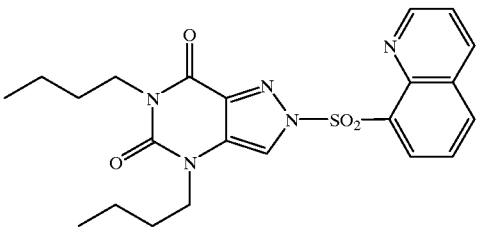

The title compound was prepared according to the procedure of example 9 except that of 8-quinolinesulfonyl chloride was used in place of propanesulfonyl chloride. Yield: 36%; mp: 203–205° C.; $^1$H NMR (300 MHz, CDCl$_3$): δ 0.89 (t, J=7.3 Hz, 3H), 1.03 (t, J=7.4 Hz, 3H), 1.26–1.81 (m, 8H), 3.89–3.97 (m, 4H), 7.51 (q, J=4.3 Hz, 1H), 7.76 (t, J=7.9 Hz, 1H), 8.12–8.27 (m, 2H), 8.52 (s, 1H), 8.78–8.90 (m, 2H); IR (KBr, cm$^{-1}$): 3136w, 2958w, 1713m, 1665s, 1625m, 1368m, 1288m, 1161m, 1072m; MS (ES) m/z (relative intensity): 456 (M$^+$+H, 100). Anal. Calcd. for $C_{22}H_{25}N_5O_4S$: C, 58.01; H, 5.53, N, 15.37. Found: C, 57.57; H, 5.40; N, 15.08

EXAMPLE 13

5,7-Dibutyl-2-(3-chloro-propane-1-sulfonyl)-2,7-dihydro-pyrazolo[3,4-d]pyrimidine-4,6-dione

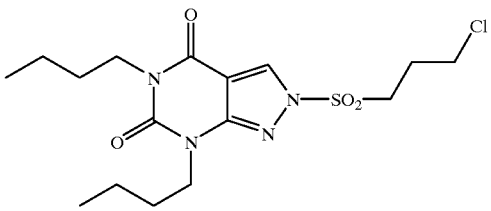

To 280 mg (1.06 mmol) of 5,7-dibutyl-1,7-dihydro-pyrazolo[3,4-d]pyrimidine-4,6-dione5,7-dione in 10 mL CH$_2$Cl$_2$ was added 0.28 mL (205 mg, 1.589 mmol) of i-Pr$_2$NEt followed by 0.14 mL (206 mg, 1.165 mmol) of 3-chloro-n-propanesulfonyl chloride. The resulting solution was stirred at 23° C. for 15 h after which time TLC shows that all starting material had been consumed. The reaction mixture was poured into brine, extracted with 2×50 mL EtOAc, and the combined organics were washed with 1×50 mL brine, dried over MgSO$_4$, filtered and evaporated to a yellow solid. Recrystallization from hot hexanes/EtOAc gave 276 mg (0.682 mmol, a 64% yield) of the title compound as an off-white solid. mp: 102–103° C.; $^1$H NMR (300 MHz, CDCl$_3$); δ 0.90–1.02 (m, 6H), 1.44 (sept, J=7.3 Hz, 4H), 1.56–1.63 (m, 2H), 1.72 (pent, J=7.6 Hz, 2H), 2.17–1.29 (m, 2H), 3.64 (t, J=5.9 Hz, 2H), 3.75 (t, J=7.4 Hz, 2H), 3.98 (t, J=7.6 Hz, 2H), 4.05 (t, J=7.4 Hz, 2H), 8.53 (s, 1H); IR (KBr, cm$^{-1}$): 3098w, 2957w, 2932w, 1720s, 1676s, 1616s, 1383m, 1166s; MS (ES) m/z (relative intensity): 405 (M$^+$+H, 100); Anal. Calcd. for C$_{16}$H$_{25}$ClN$_4$O$_4$S: C, 47.46; H, 6.22, N, 13.84. Found: C, 47.33; H, 6.13; N, 13.52.

EXAMPLE 14

5,7-Dibutyl-2-(4-trifluoromethoxy-benzenesulfonyl)-2,7-dihydro-pyrazolo[3,4-d]pyrimidine-4,6-dione

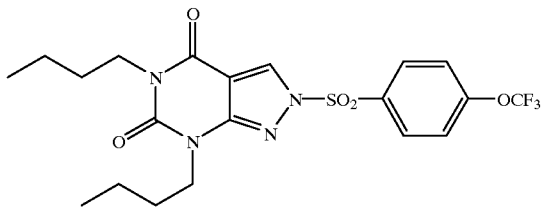

The title compound was synthesized according the procedure of example 12 except that 4-trifluoromethylbenzenesulfonyl chloride was used in place of 3-chloro-n-propanesulfonyl chloride. Yield: 79%; mp: 135–137° C.; $^1$H NMR (300 MHz, CDCl$_3$); δ 0.88–0.98 (m, 6H), 1.35 (sept, J=7.3 Hz, 4H), 1.52–1.72 (m, 4H), 3.89–4.03 (m, 4H), 7.39 (d, J=8.3 Hz, 2H), 8.12 (d, J=8.3 Hz, 2H), 8.59 (s, 1H); IR (KBr, cm$^{-1}$): 3095m, 2962m, 1715s, 1676s, 1615s, 1395s, 1268s, 1252s, 1066m; MS (ES) m/z (relative intensity): 473 (M$^+$+H, 100); Anal. Calcd. for C$_{20}$H$_{23}$F$_3$N$_4$O$_5$S: C, 49.18; H, 4.75, N, 11.47. Found: C, 49.11; H, 4.82; N, 11.27.

EXAMPLE 15

5,7-Dibutyl-2-(4,5-dichloro-thiophene-2-sulfonyl)-2,7-dihydro-pyrazolo[3,4-d]pyrimidine-4,6-dione

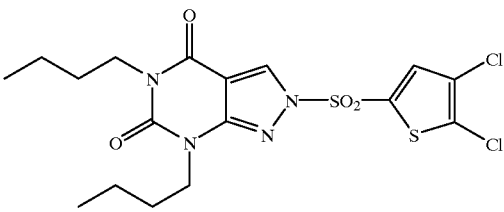

The title compound was synthesized according the procedure of example 12 except that 5-[2,3-dichlorothiophene] sulfonyl chloride was used in place of 3-chloro-n-propanesulfonyl chloride. Yield: 75%; mp: 181–182° C.; $^1$H NMR (300 MHz, CDCl$_3$); δ 0.90–1.01 (m, 6H), 1.31–1.46 (m, 4H), 1.52–1.63 (m, 2H), 1.64–1.75 (m, 2H), 3.95 (t, J=7.4 Hz, 2H), 4.04 (t, J=7.4 Hz, 2H), 7.68 (s, 1H), 8.53 (s, 1H); IR (KBr, cm$^{-1}$): 3138w, 2955m, 2932w, 1718s, 1683s, 1614s, 1390m, 1182m; MS (ES) m/z (relative intensity): 479 (M$^+$+H, 100); Anal. Calcd. for C$_{17}$H$_{20}$Cl$_2$N$_4$O$_4$S$_2$: C, 42.59; H, 4.21, N, 11.68. Found: C, 42.60; H, 4.18; N, 11.60.

EXAMPLE 16

5,7-Dibutyl-2-(4-trifluoromethyl-benzenesulfonyl)-2,7-dihydro-pyrazolo[3,4-d]pyrimidine-4,6-dione

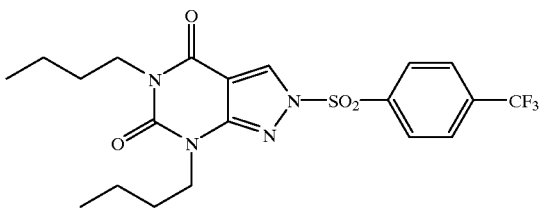

The title compound was synthesized according the procedure of example 12 except that 4-trifluoromethylbenzenesulfonyl chloride was used in place of 3-chloro-n-propanesulfonyl chloride. Yield: 87%; mp: 151–153° C.; $^1$H NMR (300 MHz, CDCl$_3$); δ 0.89–0.99 (m, 6H), 1.27–1.43 (m, 4H), 1.53–1.61 (m, 2H), 1.61–1.71 (m, 2H), 3.91 (t, J=7.4 Hz, 2H), 3.97 (t, J=7.4 Hz, 2H), 7.85 (d, J=8.4 Hz, 2H), 8.20 (d, J=8.4 Hz, 2H), 8.59 (s, 1H); IR (KBr, cm$^{-1}$): 3105w, 2961w, 2934w, 1713s, 1677s, 1615s, 1396s, 1323s, 1182s, 1063m; MS (ES) m/z (relative intensity): 473 (M$^+$+H, 100); Anal. Calcd. for C$_{20}$H$_{23}$F$_3$N$_4$O$_4$S: C, 50.84; H, 4.91, N, 11.86. Found: C, 50.79; H, 4.81; N, 11.86.

EXAMPLE 17

5,7-Dibutyl-2-methanesulfonyl-2,7-dihydro-pyrazolo[3,4-d]pyrimidine-4,6-dione

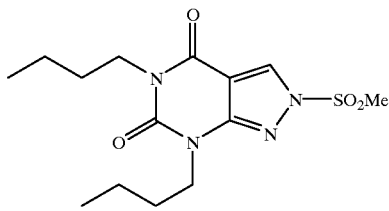

The title compound was synthesized according the procedure of example 12 except that methanesulfonyl chloride was used in place of 3-chloro-n-propanesulfonyl chloride. Yield: 76%; mp: 103–104° C.; $^1$H NMR (300 MHz, CDCl$_3$); δ 0.91–0.99 (m, 6H), 1.39 (sept, J=7.4 Hz, 4H), 1.54–1.63 (m, 2H), 1.67–1.78 (m, 2H), 3.42 (s, 3H), 3.98 (t, J=7.4 Hz, 2H), 4.05 (t, J=7.4 Hz, 2H), 8.53 (s, 1H); IR (KBr, cm$^{-1}$): 3111w, 2953w, 2927s, 1724s, 1668s, 1608s, 1378m, 768m; MS (ES) m/z (relative intensity): 343 (M$^+$+H, 100); Anal. Calcd. for C$_{14}$H$_{22}$N$_4$O$_4$S: C, 49.11; H, 6.48; N, 16.36. Found: C, 49.09; H, 6.62; N, 16.39.

EXAMPLE 18

4-Butyl-2-(3-chloro-propane-1-sulfonyl)-6-methyl-2,4-dihydro-pyrazolo[4,3-d]pyrimidine-5,7-dione

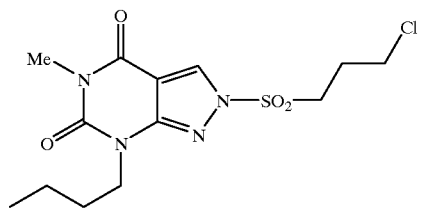

Step 1

1-Butyl-3,6-dimethyl-1H-pyrimidine-2,4-dione

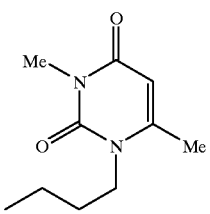

To 2.3 g (12.62 mmol) of 1-butyl-6-methyl-1H-pyrimidine-2,4-dione in 100 mL DMF was added 3.49 (25.2 mmol) of K$_2$CO$_3$, 0.98 mL (2.24 g, 15.76 mmol) of MeI and the reaction mixture was heated to 65° C. After 16.5 h, TLC (8/1 CH$_2$Cl$_2$/EtOAc) indicated the consumption of starting material (R$_f$=0.15). After cooling to 23° C., the resulting slurry was filtered through Celite, and evaporated to a yellow. This oil was dissolved in 100 mL EtOAc, extracted with 100 mL brine, 3×100 mL H$_2$O, 1×100 mL brine, dried over MgSO$_4$, filtered and evaporated to a yellow oil. Flash chromatography on silica gel, eluting with CH$_2$Cl$_2$/EtOAc (20/1 to 4/1), gave 2.03 g (10.34 mmol, an 82% yield) of the title compound as a white crystalline solid. mp: 181–182° C.; $^1$H NMR (300 MHz, CDCl$_3$): δ 0.95 (t, J=7.3 Hz, 3H), 1.38 (hex, J=7.3 Hz, 2H), 1.57–1.67 (m, 2H), 2.25 (s, 3H), 3.32 (s, 3H), 3.81 (t, J=7.4 Hz, 2H), 5.59 (s, 1H); IR (KBr, cm$^{-1}$): 3083w, 2955w, 2876w, 1702s, 1665s, 1614s, 1446s, 1435s, 1368w, 1043w; MS (ES) m/z (relative intensity): 197 (M$^+$+H, 100). Anal. Calcd. for C$_{10}$H$_{16}$N$_2$O$_2$: C, 61.20; H, 8.22; N, 14.27. Found: C, 60.95; H, 8.19; N, 14.16.

Step 2

1-Butyl-3,6-dimethyl-5-nitro-1H-pyrimidine-2,4-dione

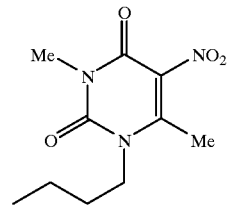

To 1.69 g (8.61 mmol) of 1-butyl-3,6-dimethyl-1H-pyrimidine-2,4-dione in 30 mL concentrated H$_2$SO$_4$ at 0° C. was added 1.7 mL fuming HNO$_3$ in drops over 10 min. After stirring at 0° C. for an additional 30 min, the reaction mixture was poured into 300 mL of ice, extracted with 2×150 mL CH$_2$Cl$_2$, and the combined organics were dried over MgSO$_4$, filtered and evaporated to a yellow oil. Flash chromatography on silica gel, eluting with CH$_2$Cl$_2$/EtOAc (40/1), gave 1.72 g (7.13 mmol, an 83% yield) of the title compound as a light yellow oil. $^1$H NMR (300 MHz, CDCl$_3$): δ 0.99 (t, J=7.3 Hz, 3H), 1.46 (hex, J=7.3 Hz, 2H), 1.62–1.73 (m, 2H), 2.42 (s, 3H), 3.39 (s, 3H), 3.92 (t, J=7.4 Hz, 2H); IR (KBr, cm$^{-1}$): 2961s, 2874s, 1722s, 1670s, 1620s, 1363s, 1224m; MS (ES) m/z (relative intensity): 242 (M$^+$+H, 100). Anal. Calcd for C$_{10}$H$_{15}$N$_3$O$_4$: C, 49.79; H, 6.27, N, 17.42. Found: C, 49.47; H, 6.03; N, 17.37.

Step 3

5-Amino-1-butyl-3,6-dimethyl-1H-pyrimidine-2,4-dione

To 1.48 g (6.14 mmol) of 1-butyl-3,6-dimethyl-5-nitro-1H-pyrimidine-2,4-dione in 60 mL EtOAc was added 500 mg of 10% Pd/C. The resulting mixture was hydrogenated under 1 atm of H$_2$ for 67 h at 23° C. The reaction mixture was then poured through Celite and the solvent evaporated to give 1.24 g (5.87 mmol, a 96% yield) of the title compound as a white solid. mp: 74–75° C.; $^1$H NMR (300 MHz, CDCl$_3$): δ 0.99 (t, J=7.3 Hz, 3H), 1.40 (hex, J=7.4 Hz, 2H), 1.56–1.67 (m, 2H), 2.22 (s, 3H), 3.39 (s, 3H), 3.84 (t, J=7.3 Hz, 2H), NH$_2$ not visible; IR (KBr, cm$^{-1}$): 3142w, 2965w, 1719s, 1679s, 1627s, 1380m, 1296m, 1166s, 1063m; MS (ES) m/z (relative intensity): 363 (M++H, 100). Anal. Calcd for $C_{10}H_{17}N_3O_2$: C, 43.03; H, 5.28; N, 15.44. Found: C, 43.11; H, 5.33; N, 15.26.

Step 4

4-Butyl-6-methyl-1,4-dihydro-pyrazolo[4,3-d]pyrimidine-5,7-dione

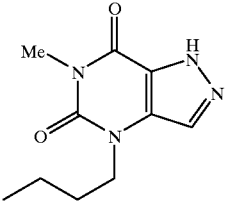

To 1.03 g (4.88 mmol) of 5-amino-1-butyl-3,6-dimethyl-1H-pyrimidine-2,4-dione in 20 mL $H_2O$ and 5 mL conc HCl at 0° C. was added a solution of 320 mg (4.64 mmol) of $NaNO_2$ and 3 mL $H_2O$ in drops such that the internal reaction temperature does not exceed 5° C. (10 min). After stirring for an additional 10 min, the resulting slurry was added in drops to a 0° C. solution of 20% aq. NaOH. After addition is complete, the resulting solution is stirred at 23° C. for 20 min, neutralized to pH ~7 with dilute aq. HCl, poured into 200 mL of pH 7 buffer, and extracted with 2×150 mL EtOAc. The combined organics were dried over $Na_2SO_4$, filtered and evaporated to an orange solid. Flash chromatography on silica gel, eluting with $CH_2Cl_2$/EtOAc (20/1 to 4/1), gave 617 mg (2.78 mmol, a 57% yield) of the title compound as an off-white solid. mp: 160–162° C.; $^1$H NMR (300 MHz, $CDCl_3$): δ 0.98 (t, J=7.4 Hz, 3H), 1.44 (hex, J=7.3 Hz, 2H), 1.71–1.80 (m, 2H), 3.47 (s, 3H), 3.95 (t, J=7.4 Hz, 2H), 7.56 (s, 1H); IR (KBr, cm$^{-1}$): 3142w, 2953w, 2932w, 1708s, 1649s, 1610s, 1296w; MS (ES) m/z (relative intensity): 223 (M++H, 100). Anal. Calcd for $C_{10}H_{14}N_4O_2$: C, 54.04; H, 6.35; N, 25.21. Found: C, 52.50; H, 6.23; N, 22.64.

Step 5

4-Butyl-2-(3-chloro-propane-1-sulfonyl)-6-methyl-2,4-dihydro-pyrazolo[4,3-d]pyrimidine-5,7-dione

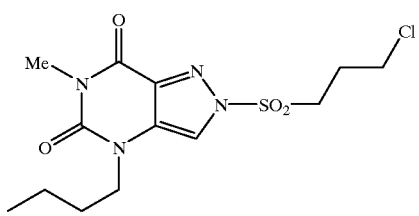

The title compound was synthesized according to the procedure of example 1 except that 4-butyl-6-methyl-1,4-dihydro-pyrazolo[4,3-d]pyrimidine-5,7-dione was used in place of 4,6-dibutyl-1,4-dihydro-pyrazolo[4,3-d]pyrimidine-5,7-dione. Yield: 72%; mp: 105–106° C.; $^1$H NMR (300 MHz, $CDCl_3$): δ 0.98 (t, J=7.3 Hz, 3H), 1.41 (hex, J=7.3 Hz, 2H), 1.63–1.78 (m, 2H), 2.20–2.34 (m, 2H), 3.60 (s, 3H), 3.64 (t, J=7.4 Hz, 2H), 3.81–3.91 (m, 4H), 7.89 (s, 1H); IR (KBr, cm$^{-1}$): 3142w, 2950w, 2870w, 1719s, 1679s, 1626m, 1380m, 1296m, 1165s, 1063m; MS (ES) m/z (relative intensity): 363 (M++H, 100). Anal. Calcd. for $C_{13}H_{19}ClN_4O_4S$: C, 43.03; H, 5.28; N, 15.44. Found: C, 43.11; H, 5.33; N, 15.26.

EXAMPLE 19

5,7-Dibutyl-2-phenylmethanesulfonyl-1,7-dihydro-pyrazolo[3,4-d]pyrimidine-4,6-dione

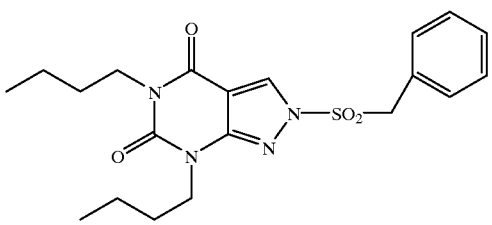

The title compound was prepared according to the procedure of example 7, step 2 except that benzylsulfonyl chloride was used in place of of 5-chloro-1,3-dimethylpyrazole-4-sulfonyl chloride. Yield: 11%; mp: 137–140° C.; $^1$H NMR (300 MHz, $CDCl_3$): δ 0.94 (t, J=7.3 Hz, 3H), 1.01 (t, J=7.3 Hz, 3H), 1.33–1.46 (m, 4H), 1.49–1.63 (m, 2H), 1.75–1.83 (m, 2H) 3.95 (t, J=7.5 Hz, 2H), 4.10 (t, J=7.4 Hz, 2H) ,4.75 (s, 2H), 7.06–7.26 (dd, J=10.8, 2.1 Hz, 2H) 7.26–7.61 (m, 3H), 8.07 (s, 1H); IR (KBr, cm$^{-1}$): 3125w, 2961m, 2934w, 2873w 1777s, 1716s, 1649s, 1541w, 1379s, 1276m, 1162s, 1066m, 767w; MS (ES) m/z (relative intensity): 419 (M++H, 100). Anal. Calcd. for $C_{20}H_{26}N_4O_4S$: C, 57.40; H, 6.26; N, 13.39. Found: C, 57.59; 5 H, 6.28; N, 13.17.

EXAMPLE 20

6-Butyl-2-(3-chloro-propane-1-sulfonyl)-4-(3-methyl-butyl)-2,4-dihydro-pyrazolo[4,3-d]pyrimidine-5,7-dione

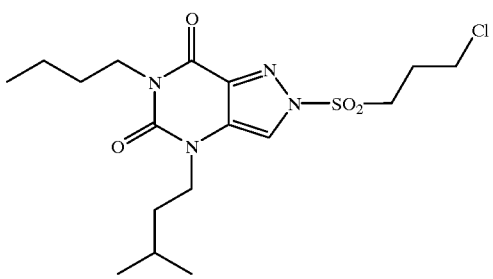

Step 1

3-Butyl-1-(3-methyl-butyl)-6-methyluracil

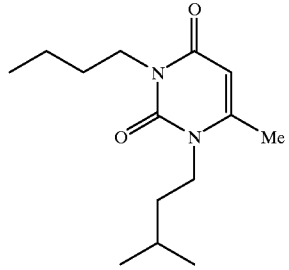

To 5.0 g (27 mmol) of 3-butyl-6-methyluracil in 100 mL of acetone was added 14.9 g (108 mmol) of $K_2CO_3$ followed by 4.07 g (27 mmol) of 1-bromo-3-methyl butane. The resulting mixture was refluxed for 48 h. After cooling to 23° C., the reaction mixtyre was filtered and evaporated to give the 8.2 g (24 mmol, a 91% yield) of the title compound as a yellow oil. Yield 91%.; $^1$H NMR (300 MHz, $CDCl_3$); δ 0.91–0.98 (m, 6H), 1.25 (s, 3H), 1.32–1.40 (m, 2H), 1.48–1.80 (m, 5H), 2.15 (s, 3H), 3.67–3.83 (m, 2H), 3.88–3.96 (m, 2H) 5.57 (s, 1H); IR (KBr, $cm^{-1}$): 3476w, 2958w, 2933w, 2872m, 1701s, 1538m, 1432m, 1364m; MS (ES) m/z (relative intensity): 253 ($M^+$+H).

Step 2

3-Butyl-6-methyl-1-(3-methyl-butyl)-5-nitro-1H-pyrimidine-2,4-dione

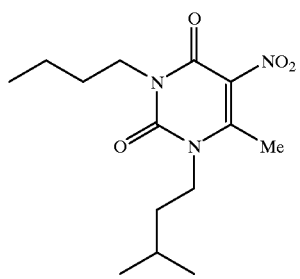

The title compound was prepared according to the procedure of example 18, step 2 except that 3-butyl-1-(3-methyl-butyl)-6-methyluracil was used in place of 1-butyl-3,6-dimethyl-1H-pyrimidine-2,4-dione. Yield: 70%; $^1$H NMR (300 MHz, $CDCl_3$); δ 0.91–0.98 (m, 6H), 1.25 (s, 3H), 1.32–1.40 (m, 2H), 1.48–1.80 (m, 5H), 2.15 (s, 3H), 3.67–3.83 (m, 2H), 3.88–3.96 (m, 2H)),; IR (KBr, $cm^{-1}$): 3476w, 2958w, 2933w, 2872m, 1701s, 1538m, 1432m, 1364m; MS (ES) m/z (relative intensity): 298 ($M^+$+H). Anal. Calcd. for $C_{14}H_{23}N_3O_4$: C, 56.55; H, 7.80, N, 14.13. Found: C, 56.32; H, 7.81; N, 14.08

Step 3

5-Amino-3-butyl-6-methyl-1-(3-methyl-butyl)-1H-pyrimidine-2,4-dione

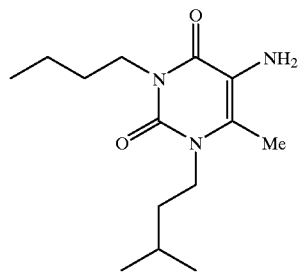

The title compound was prepared according to the procedure of example 18, step 3 except that 3-butyl-6-methyl-1-(3-methyl-butyl)-5-nitro-1H-pyrimidine-2,4-dione was used in place of 1-butyl-3,6-dimethyl-5-nitro-1H-pyrimidine-2,4-dione. Yield: 100%; mp: 68–70° C.; $^1$H NMR (300 MHz, $CDCl_3$); δ 0.91–0.98 (m, 6H), 1.25 (s, 3H), 1.32–1.40 (m, 2H), 1.48–1.80 (m, 5H), 2.15 (s, 3H), 3.21 (m, 2H) 3.67–3.83 (m, 2H), 3.88–3.96 (m, 2H); IR (KBr, $cm^{-1}$): 3435w, 3414w, 2959w, 2930w, 2869m, 1683s, 1644s, 1589m,1488m, 1359m; MS (ES) m/z (relative intensity): 268 ($M^+$+H). Anal. Calcd. for $C_{14}H_{25}N_3O_2$: C, 62.89; H, 9.42, N, 15.72. Found: C, 62.76; H, 9.23; N, 15.59.

Step 4

6-Butyl-4-(3-methyl-butyl)-1,4-dihydro-pyrazolo[4,3-d]pyrimidine-5,7-dione

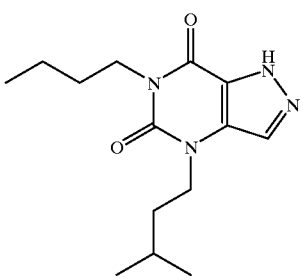

The title compound was prepared according to the procedure of example 18, step 4 except that 5-amino-3-butyl-6-methyl-1-(3-methyl-butyl)-1H-pyrimidine-2,4-dione was used in place of 5-amino-1-butyl-3,6-dimethyl-1H-pyrimidine-2,3-dione. Yield: 13%; mp: 122–124° C.; $^1$H NMR (300 MHz, $CDCl_3$); δ 0.91–1.01 (m, 9H), 1, 1.34–1.47 (m, 2H), 1.60–1.76 (m, 5H), 3.95–4.0 (m, 2H), 4.04–4.09 (m, 2H), 7.57 (s, 1H),12.5 (m, 1H) NH: IR (KBr, $cm^{-1}$): 3136m, 2958w, 2933w, 2873m, 1713s, 1612m, 1432m, 1364m; MS (ES) m/z (relative intensity): 279 ($M^+$+H). Anal. Calcd. for $C_{14}H_{22}N_4O_2$: C, 60.41; H, 7.97, N, 20.13. Found: C, 60.45; H, 8.06; N, 19.68.

Step 5

6-Butyl-4-(3-methyl-butyl)-1,4-dihydro-pyrazolo[4,3-d]pyrimidine-5,7-dione

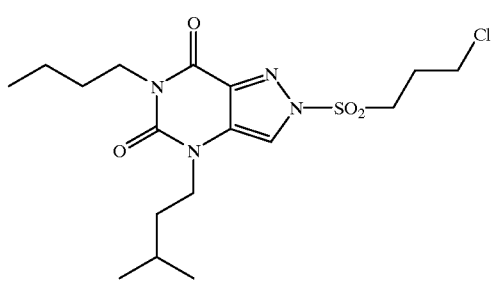

The title compound was prepared according to the procedure of example 1 except that 6-butyl-4-(3-methyl-butyl)-1,4-dihydro-pyrazolo[4,3-d]pyrimidine-5,7-dione was used in place of 4,6-dibutyl-1,4-dihydro-pyrazolo[4,3-d]pyrimidine-5,7-dione. Yield: 70%; mp: 77–79° C.; $^1$H NMR (300 MHz, CDCl$_3$); δ 0.93–1.01 (m, 9H), 1.33–1.43 (m, 2H), 1.56–1.74 (m, 5H), 2.23–2.32 (m, 2H), 3.63–3.67 (t, J=6.2 Hz, 2H), 3.82–3.89 (m, 4H) 4.03–4.07 (t, J=7.2 Hz, 2H), 7.84 (s, 1H); IR (KBr, cm$^{-1}$): 3132w, 2961w, 2936w, 2872m, 1715s, 1623m, 1379m, 1364m; MS (ES) m/z (relative intensity): 419 (M$^+$+H). Anal. Calcd. for $C_{17}H_{27}ClN_4O_4S$: C, 48.74; H, 6.50, N, 13.37. Found: C, 48.64; H, 6.40; N, 13.40.

EXAMPLE 21

2-(3-Chloro-propane-1-sulfonyl)-5,7-dimethyl-2,7-dihydro-pyrazolo[3,4-d]pyrimidine-4,6-dione

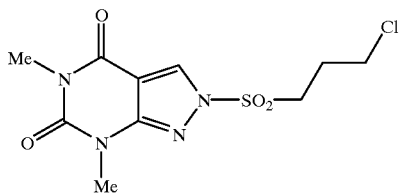

The title compound was prepared according to the procedure of example 1 except that 5,7-dimethyl-1,7-dihydro-pyrazolo[3,4-d]pyrimidine-4,6-dione was used in place of 4,6-dibutyl-1,4-dihydro-pyrazolo[4,3-d]pyrimidine-5,7-dione. Yield: 41%; mp: 160–162° C.; $^1$H NMR (300 MHz, DMSO-d$_6$): δ 2.03 (pent, J=7.2 Hz, 2H), 3.22 (s, 3H), 3.29–3.40 (m, 2H), 3.40 (s, 3H), 3.66 (t, J=7.4 Hz, 2H), 3.90–3.97 (m, 2H), 9.05 (s, 1H); IR (KBr, cm$^{-1}$): 3101m, 2973vw, 1726s, 1671s, 1606s, 1383w; MS (ES) m/z (relative intensity): 321 (M$^+$+H, 100). Anal. Calcd. for $C_{10}H_{13}ClN_4O_4S$: C, 37.45; H, 4.09, N, 17.47. Found: C, 37.55; H, 4.04; N, 17.37.

EXAMPLE 22

2-(3-Chloro-propane-1-sulfonyl)-5,7-bis-cyclopropylmethyl-2,7-dihydro-pyrazolo[3,4-d]pyrimidine-4,6-dione

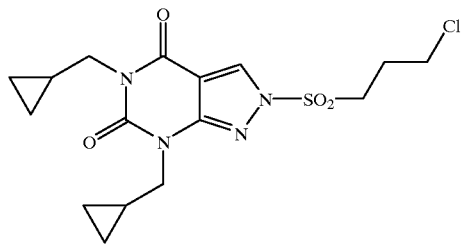

The title compound was prepared according to the procedure of example 1 except that 1,3-bis-cyclopropylmethyl-3,7-dihydro-purine-2,6-dione was used in place of 4,6-dibutyl-1,4-dihydro-pyrazolo[4,3-d]pyrimidine-5,7-dione. Yield: 47%; mp: 95–97° C.; $^1$H NMR (300 MHz, CDCl$_3$): δ 0.41–0.70 (complex m, 8H), 1.21–1.32 (m, 1H), 1.32–1.46 (m, 1H), 2.19–2.29 (m, 2H), 3.62 (t, J=7.4 Hz, 2H), 3.74 (t, J=7.4 Hz, 2H), 3.89 (d, J=7.2 Hz, 2H), 3.95 (d, J=7.2 Hz, 2H), 8.56 (s, 1H); IR (KBr, cm$^{-1}$): 3085w, 2947w, 2879w, 1717s, 1676s, 1620s, 1383s, 1265s, 1185m; MS (ES) m/z (relative intensity): 401 (M$^+$+H, 100). Anal. Calcd. for $C_{16}H_{21}ClN_4O_4S$: C, 47.94; H, 5.28, N, 13.98. Found: C, 47.54; H, 5.30; N, 13.79.

We claim:
1. A compound of formula (I)

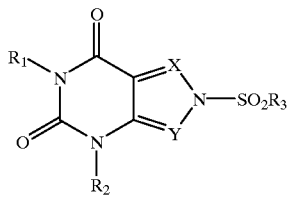

(I)

wherein:

X=N and Y=CH or X=CH and Y=N $R_1$ and $R_2$ are independently, straight chain alkyl of 2 to 12 carbon atoms, branched chain alkyl of 3 to 10 carbon atoms, cycloalkyl of 3 to 10 carbon atoms, aryl of 6 to 10 carbon atoms, 6 to 10 membered heteroaryl or a moiety of the formula —(CH$_2$)$_m$-A wherein m is 1 to 9 and A is cycloalkyl of 3 to 7 carbon atoms; and $R_3$ is a straight chain alkyl of 1 to 12 carbon atoms, branched chain alkyl of 3 to 10 carbon atoms, aryl of 6 to 10 carbon atoms or 6 to 10 membered heteroaryl; or a pharmaceutically acceptable salt thereof.

2. A compound according to claim 1 of formula (I) wherein: $R_1$ and $R_2$, are independently, straight chain alkyl of 2 to 6 carbon atoms or branched chain alkyl of 3 to 6 carbon atoms; and $R_3$ is a straight chain alkyl of 3 to 6 carbon atoms, aryl of 4 to 10 carbon atoms or 4 to 10 membered heteroaryl; or a pharmaceutically acceptable salt thereof.

3. A compound of claim 1 which is 4,6-dibutyl-3-chloropropanesulfonyl-2,4-dihydro-pyrazolo[4,3-d]pyrimidine-5,7-dione or a pharmaceutically acceptable salt thereof.

4. A compound of claim 1 which is 4,6-dibutyl-2-phenylmethanesulfonyl-2,4-dihydro-pyrazolo[4,3-d]pyrimidine-5,7-dione or a pharmaceutically acceptable salt thereof.

5. A compound of claim 1 which is 4,6-dibutyl-2-(3-trifluoromethyl-benzene-sulfonyl)-2,4-dihydro-pyrazolo[4,3-d]pyrimidine-5,7-dione or a pharmaceutically acceptable salt thereof.

6. A compound of claim 1 which is 4,6-dibutyl-2-(2-naphthalenesulfonyl)-2,4-dihydro-pyrazolo[4,3-d]pyrimidine-5,7-dione or a pharmaceutically acceptable salt thereof.

7. A compound of claim 1 which is 4,6-dibutyl-2-(4-tert-butyl-benzenesulfonyl)-2,4-dihydro-pyrazolo[4,3-d]pyrimidine-5,7-dione or a pharmaceutically acceptable salt thereof.

8. A compound of claim 1 which is 4,6-dibutyl-2-(4,5-dichloro-thiophene-2-sulfonyl)-2,4-dihydro-pyrazolo[4,3-d]pyrimidine-5,7-dione or a pharmaceutically acceptable salt thereof.

9. A compound of claim 1 which is 4,6-dibutyl-2-(4[1,3-dimethyl-5-chloro-pyrazolsulfonyl)-2,4-dihydro-pyrazolo[4,3-d]pyrimidine-5,7-dione or a pharmaceutically acceptable salt thereof.

10. A compound of claim 1 which is 4,6-dibutyl-1-(3,5-dimethyl-isoxazole-4-sulfonyl)-1,4-dihydro-pyrazolo[4,3-d]pyrimidine-5,7-dione or a pharmaceutically acceptable salt thereof.

11. A compound of claim 1 which is 4,6-dibutyl-1-(propane-1-sulfonyl)-1,4-dihydro-pyrazolo[4,3-d]pyrimidine-5,7-dione or a pharmaceutically acceptable salt thereof.

12. A compound of claim 1 which is 4,6-dibutyl-1-ethanesulfonyl-1,4-dihydro-pyrazolo[4,3-d]pyrimidine-5,7-dione or a pharmaceutically acceptable salt thereof.

13. A compound of claim 1 which is 4,6-dibutyl-2-(2,4,6-trichlorobenzene-sulfonyl)-2,4-dihydro-pyrazolo[4,3-d]pyrimidine-5,7-dione or a pharmaceutically acceptable salt thereof.

14. A compound of claim 1 which is 4,6-dibutyl-2-(quinoline-8-sulfonyl)-2,4-hydro-pyrazolo[4,3-d]pyrimidine-5,7-dione or a pharmaceutically acceptable salt thereof.

15. A compound of claim 1 which is 5,7-dibutyl-2-(3-chloro-propane-1-sulfonyl)-2,7-dihydro-pyrazolo[3,4-d]pyrimidine-4,6-dione or a pharmaceutically acceptable salt thereof.

16. A compound of claim 1 which is 5,7-dibutyl-2-(4-trifluoromethoxybenzene-sulfonyl)-2,7-dihydro-pyrazolo[3,4-d]pyrimidine-4,6-dione or a pharmaceutically acceptable salt thereof.

17. A compound of claim 1 which is 5,7-dibutyl-2-(4,5-dichloro-thiophene-2-sulfonyl)-2,7-dihydro-pyrazolo[3,4-d]pyrimidine-4,6-dione or a pharmaceutically acceptable salt thereof.

18. A compound of claim 1 which is 5,7-dibutyl-2-(4-trifluoromethylbenzene-sulfonyl)-2,7-dihydro-pyrazolo[3,4-d]pyrimidine-4,6-dione or a pharmaceutically acceptable salt thereof.

19. A compound of claim 1 which is 5,7-dibutyl-2-methanesulfonyl-2,7-dihydro-pyrazolo[3,4-d]pyrimidine-4,6-dione or a pharmaceutically acceptable salt thereof.

20. A compound of claim 1 which is 4-butyl-2-(3-chloro-propane-1-sulfonyl)-6-methyl-2,4-dihydro-pyrazolo[4,3-d]pyrimidine-5,7-dione or a pharmaceutically acceptable salt thereof.

21. A compound of claim 1 which is 5,7-dibutyl-2-phenylmethanesulfonyl-1,7-dihydro-pyrazolo[3,4-d]pyrimidine-4,6-dione or a pharmaceutically acceptable salt thereof.

22. A compound of claim 1 which is 6-butyl-2-(3-chloro-propane-1-sulfonyl)-4-(3-methyl-butyl)-2,4-dihydro-pyrazolo[4,3-d]pyrimidine-5,7-dione or a pharmaceutically acceptable salt thereof.

23. A compound of claim 1 which is 2-(3-chloro-propane-1-sulfonyl)-5,7-bis-cyclopropylmethyl-2,7-dihydro-pyrazolo[3,4-d]pyrimidine-4,6-dione or a pharmaceutically acceptable salt thereof.

24. A method of stimulating endogenous calcitonin synthesis in a patient suffering from a condition associated with bone loss comprising administering a therapeutically effective amount of a compound of formula (I):

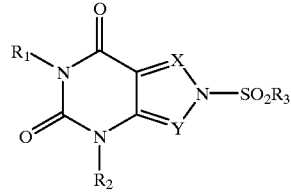

wherein:

X=N and Y=CH or X=CH and Y=N $R_1$ and $R_2$ are independently, straight chain alkyl of 1 to 12 carbon atoms, branched chain alkyl of 3 to 10 carbon atoms, cycloalkyl of 3 to 10 carbon atoms, aryl of 6 to 10 carbon atoms, 6 to 10 membered heteroaryl or a moiety of the formula —$(CH_2)_m$-A wherein m is 1 to 9 and A is cycloalkyl of 3 to 7 carbon atoms; and $R_3$ is a straight chain alkyl of 1 to 12 carbon atoms, branched chain alkyl of 3 to 10 carbon atoms, aryl of 4 to 10 carbon atoms or 4 to 10 membered heteroaryl; or a pharmaceutically acceptable salt thereof.

25. The method of claim 24 where the condition associated with bone loss is Paget's Disease, post menopausal osteoporosis, senile osteoporosis or glucocorticoid-induced osteoporosis.

26. A pharmaceutical composition comprising a therapeutically effective amount of a compound of formula (I):

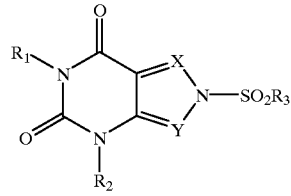

wherein:

X=N and Y=CH or X=CH and Y=N $R_1$ and $R_2$ are independently, straight chain alkyl of 1 to 12 carbon atoms, branched chain alkyl of 3 to 10 carbon atoms, cycloalkyl of 3 to 10 carbon atoms, aryl of 6 to 10 carbon atoms, 6 to 10 membered heteroaryl or a moiety of the formula —$(CH_2)_m$-A wherein m is 1 to 9 and A is cycloalkyl of 3 to 7 carbon atoms; and $R_3$ is a straight chain alkyl of 1 to 12 carbon atoms, branched chain alkyl of 3 to 10 carbon atoms, aryl of 4 to 10 carbon atoms or 4 to 10 membered heteroaryl; or a pharmaceutically acceptable salt thereof; and a pharmaceutically acceptable carrier.

* * * * *